US007666988B1

(12) United States Patent
Defrenne et al.

(10) Patent No.: US 7,666,988 B1
(45) Date of Patent: Feb. 23, 2010

(54) BASB082 POLYPEPTIDES

(75) Inventors: Catherine Defrenne, Rixensart (BE); Christine Delmelle, Rixensart (BE); Jean-Louis Ruelle, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 09/936,377

(22) PCT Filed: Mar. 7, 2000

(86) PCT No.: PCT/EP00/01955

§ 371 (c)(1),
(2), (4) Date: Feb. 26, 2002

(87) PCT Pub. No.: WO00/55327

PCT Pub. Date: Sep. 21, 2000

(30) Foreign Application Priority Data

| Mar. 12, 1999 | (GB) | 9905815.8 |
| Apr. 21, 1999 | (GB) | 9909094.6 |
| Apr. 23, 1999 | (GB) | 9909503.6 |
| Apr. 28, 1999 | (GB) | 9909787.5 |
| May 7, 1999 | (GB) | 9910710.4 |

(51) Int. Cl.
C07K 14/22 (2006.01)
C07K 1/00 (2006.01)
C07H 21/04 (2006.01)
C12N 1/20 (2006.01)
A61K 39/095 (2006.01)
A61K 39/02 (2006.01)

(52) U.S. Cl. ............. 530/350; 530/300; 424/250.1; 424/249.1; 424/190.1; 424/184.1; 435/69.3; 435/252.3; 536/23.1; 536/23.7; 536/24.32

(58) Field of Classification Search ............. 424/184.1, 424/185.1, 190.1, 249.1, 250.1; 530/300, 530/350; 536/23.1, 23.7, 24.1, 24.32; 435/69.1, 435/69.3, 243, 252.3, 223
See application file for complete search history.

(56) References Cited

U.S. PATENT DOCUMENTS

2005/0191316 A1  9/2005  Fraser et al.
2007/0026021 A1  2/2007  Fraser et al.

FOREIGN PATENT DOCUMENTS

| WO | WO96/12020 | 4/1996 |
| WO | WO98/02547 | 1/1998 |
| WO | WO99/24578 | 5/1999 |
| WO | WO99/57280 | 11/1999 |
| WO | WO 00/22430 A3 | 4/2000 |
| WO | WO00/66791 | 11/2000 |
| WO | WO01/85772 | 11/2001 |

OTHER PUBLICATIONS

Rudinger et al, in "Peptide Hormones", edited by Parsons, J.A., University Park Press, Jun. 1976, p. 6).*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67).*
Unanue. ER 1999 , American Journal of Pathology; 154; 651-664).*
Infect Immun. Jul. 1998;66(7):3223-31.*
Molloy et al (Molecular Immunol. 35, 1998, pp. 73-81).*
Arnon et al Faseb J. Nov. 1992; 6(14): 3265-74).*
Roitt et al, 1998, Immunology, 4th ed, Mosby, p. 7.7-7.8.*
Holmes (Exp. Opin.Invest. Drugs, 2001, 10(3):511-519.*
Herbert et al. (The Dictionary of Immunology, Academic Press, 4th edition, 1995, p. 58-59.*
Greenspan et al (Nature Biotechnology 7:936-937 (1999).*
Bowie et al (Science, 1990, 257:1306-1310.*
Coleman et al. (Research in Immunology, 1994; 145(1): 33-36).*
Abaza et al. (Journal of Protein Chemistry, vol. 11, No. 5, 1992, pp. 433-444.*
Lederman et al (Molecular Immunology 28:1171-1181, 1991).*
Li et al (Proc. Natl. Acad. Sci. USA 77:3211-3214, 1980).*
Herbert et al (The Dictionary of Immunology, Academic Press, 3rd Edition, London, 1985, pp. 58.*
Martin D et al: "Highly Conserved *Neisseria meningitidis* Surface Protein Confers Protection Against Experimental Infection" Journal of Experimental Medicine, vol. 185, No. 7, (1997), pp. 1173-1183.
Lissolo L et al: "Evaluation of Transferrin-Binding Protein 2 with the Transferrin Binding Protein Complex as a Potential Antigen for Future Meningococcal Vaccines" Infection and Immunity, vol. 63, No. 3, Mar. 1995, pp. 884-890.
International Search Report from PCT/EP00/01955.
"Selection of Immunogenic Peptides for Antisera Production," *Current Protocols in Immunology*, John Wiley & Sons, 1991, units 9.3.1-9.3.5..
Geysen et al., "Use of peptide synthesis to probe viral antigens for epitopes to a resolution of a single amino acid," *Proc. Nat. Acad. Sci. USA*, Jul. 1984, vol. 81, pp. 3998-4002.
Reece et al., "Scanning for T helper epitopes with human PBMC using pools of short synthetic peptides," *Journal of Immunological Methods*, 1994, vol. 172, No. 2, pp. 241-254.
Reece et al., "Mapping the Major Human T Helper Epitopes of Tetanus Toxin," *The Journal of Immunology*, 1993, vol. 151, pp. 6175-6184.
"Synthesis of Multipe Peptides on Plastic Pins," *Current Protocols in Immunology*, John Wiley & Sons, 1997, units 9.7.1-9.7.19.

(Continued)

*Primary Examiner*—Robert B Mondesi
*Assistant Examiner*—Padma Baskar
(74) *Attorney, Agent, or Firm*—Seed IP Group PLLC

(57) ABSTRACT

The invention provides BASB082, BASB083, BASB091, BASB092 and BASB101 polypeptides and polynucleotides encoding BASB082, BASB083, BASB091, BASB092 and BASB101 polypeptides and methods for producing such polypeptides by recombinant techniques. Also provided are diagnostic, prophylactic and therapeutic uses.

23 Claims, 5 Drawing Sheets

OTHER PUBLICATIONS

Niman, et al., "Generation of protein-reactive antibodies by short peptides is an event of high frequency: Implications for the structural basis of immune recognition," *Proc. Natl. Acad. Sci. USA*, Aug. 1983, vol. 80, pp. 4949-4953.

Dillner et al., "Antibodies against a synthetic peptide identify the Epstein-Barr virus-determined nuclear antigen," Aug. 1984, *Proc. Natl. Acad. Sci. USA*, vol. 81, pp. 4652-4656.

Sali et al., "Three-dimensional Models of four Mouse Mast Cell Chymases," *The Journal of Biological Chemistry*, vol. 268, No. 12, Apr. 25, 1993, pp. 9023-9034.

Tettelin et al., "Complete Genome Sequence of *Neisseria meningitidis* Serogroup B Strain MC58," *Science*, vol. 287, Mar. 10, 2000, pp. 1809-1815.

Zhou et al., "On the origin of membrane vesicles in Gram-negative bacteria," *Ferns Microbiology Letter*, 163, 1998, pp. 223-238.

Shinnick et al., "Synthetic Peptide Immunogens as Vaccines," *Annual Review Microbiology*, 1983, vol. 37, pp. 425-446.

Geysen et al., "Small peptides induce antibodies with a sequence and structural requirement for binding antigen comparable to antibodies raised against the native protein," *Proc. Natl. Acad. Sci. USA*, vol. 82, Jan. 1985, pp. 178-182.

Roitt et al., "The Structures of Antigens," *Immunology*, 3d Edition, 1993, units 7.7-7.8.

Peeters et al., "Phase I clinical trial with a hexavalent PorA containing meningococcal outer membrane vesical vaccine," *Vaccine*, vol. 14, No. 10, 1996, pp. 1009-1015.

Claassen et al., "Production, characterization and control of a *Neisseria meningitidis* hexavalent class 1 outer membrane protein containing vesicle vaccine," *Vaccine*, vol. 14, No. 10, 1996, pp. 1001-1008. •.

Fredriksen et al., "Production, characterization and control of MenB-vaccine "Folkehelsa": an outer membrane vesicle vaccine against group B meningococcal disease," *NIPH Annals*, vol. 14, No. 2, Dec. 1991, pp. 67-80.

Hopp, "Retrospective: 12 Years of Antigenic Determinant Predictions, and More," *Peptide Research* 6(4):183-190, 1993.

Jameson et al., "The antigenic index: a novel algorithm for predicting antigenic determinants," *Computer Application Bioscience* 4(1):181-186, 1988.

Kolaskar et al., "A semi-empirical method for prediction of antigenic determinants on protein antigens," *FEBS* 276(1,2):172-174, 1990.

Menéndez-Arias et al., "A BASIC microcomputer program for prediction of B and T cell epitopes in proteins," *Comput. Appl. Biosci.* 6(2):101-105, 1990.

Parkhill et al., "Complete DNA sequence of a serogroup a strain of *Neisseria meningitidis* Z2491," *Nature* 404:502-506, 2000.

Roitt et al., *Immunology*, 4th Edition, 1998, pp. 7.7-7.8, Mosby, London.

Rokbi et al., "Evaluation of Recombinant Transferrin-Binding Protein B Variants from *Neisseria meningitidis* for Their Ability To Induce Cross-Reactive and Bactericidal Antibodies against a Genetically Diverse Collection of Serogroup B Strains," *Infection and Immunity* 65(1):55-63, 1997.

Thornton et al., "Location of 'continuous' antigenic determinants in the protruding regions of proteins," *EMBO Journal* 5(2):409-413, 1986.

* cited by examiner

Figure 1A

SEQ ID NO:1

*Neisseria meningitidis* BASB082 polynucleotide sequence from strain ATCC 13090

ATGGCACAAACTACACTCAAACCCATTGTTTTATCAATTCTTTTAATCAACACACCCCTC
CTCGCCCAAGCGCATGAAACTGAGCAATCGGTGGGCTTGGAAACGGTTACCGTCGTCGGC
AAAAGCCGTCCGCGCGCCACATCAGGGCTGCTGCACACTTCGACCGCCTCCGACAAAATC
ATCAGCGGCGACACCTTGCGACAAAAAGCCGTCAACTTGGGCGATGCTTTGGACGGCGTG
CCGGGCATTCACGCCTCGCAATACGGCGGCGGCGCGTCCGCTCCCGTTATTCGCGGTCAA
ACAGGCAGACGGATTAAAGTATTGAACCATCACGGCGAAACAGGCGATATGGCGGATTTT
TCGCCCGATCACGCCATTATGGTAGATACCGCCTTGTCGCAACAGGTCGAAATCCTGCGC
GGGCCGGTTACGCTCTTGTACAGCTCGGGCAATGTGGCGGGGCTGGTCGATGTTGCCGAT
GGCAAAATCCCCGAAAAAATGCCTGAAAACGGCGTATCGGGCGAACTCGGATTGCGTTTG
AGCAGCGGCAATCTGGAAAAACTCACGTCCGGCGGCATCAATATCGGTTTGGGCAAAAAC
TTTGTATTGCACACGGAAGGGCTGTACCGCAAATCGGGGGATTACGCCGTACCGCGTTAC
CGCAATCTGAAACGCCTGCCCGACAGCCCACGCCGATTCGCAAACGGGCAGCATCGGGCT
GTCTTGGGTTGGCGAAAAAGGTTTTATCGGCGTACGTACAGCGACCGTCGCGACCAATAT
GGTCTGCCTGCCCACAGCCACGAATACGATGATTGCCACGCCGACATCATCTGGCAAAAG
AGCTTGATTAACAAACGCTATTTACAGCTTTATCCGCACCTGTTGACCGAAGAAGACGTC
GATTACGACAATCCGGGCTTGAGCTGCGGCTTCCACGACGACGATGATGCACACGCCCAT
GCCCACAACGGCAAACCTTGGATAGACCTGCGCAACAAACGCTACGAACTCCGCGCCGAA
TGGAAGCAGCCATTCCCCGGTTTTGAAGCCCTGCGCGTACACCTGAACCGCAACGACTAC
CACCACGACGAAAAAGCAGGCGATGCAGTCGAAAACTTTTTTAACAACCAAACGCAAAAC
GCCCGCATCGAGTTGCGCCACCAACCCATAGGCCGTCTGAAAGGCAGCTGGGGCGTGCAA
TATTTGGGACAAAAATCCAGTGCTTTATCTGCCACATCCGAAGCGGTCAAACAACCGATG
CTGCTTGACAATAAAGTGCAACATTACAGCTTTTTCGGTGTAGAACAGGCAAACTGGGAC
AACTTCACGCTTGAAGGCGGCGTACGCGTGGAAAAACAAAAAGCCTCCATCCGCTACGAC
AAAGCATTGATTGATCGGGAAAACTACTACAAGCAGCCCCTGCCCGACCTCGGCGCGCAC
CGCCAAACCGCCCGCTCGTTCGCACTTTCGGGCAACTGGTATTTCACGCCGCAACACAAA
CTCAGCCTGACCGCCTCCCATCAGGAACGCCTGCCGTCAACGCAAGAGCTGTACGCACAC
GGCAAACACGTTGCCACCAACACTTTTGAAGTCGGCAACAAACACCTGAACAAAGAGCGT
TCCAACAACATCGAACTCGCGTTGGGCTACGAAGGCGACCGCTGGCAATACAATCTGGCA
CTCTACCGCAACCGCTTCGGCAACTACATTTACGCCCAAACCTTAAACGACGGACGCGGC
CCCAAATCCATCGAAGACGACAGCGAAATGAAGCTCGTGCGCTACAACCAATCCGGTGCG
GACTTCTACGGCGCGGAAGGCGAAATCTACTTCAAACCGACACCGCGCTACCGCATCGGC
GTTTCCGGCGACTATGTACGAGGCCGTCTGAAAAACCTGCCGTCCCTACCCGGCAGGGAA
GATGCCTACGGCAACCGTCCTTTCATCGCGCAGGACGACCAAAACGCCCCTCGCGTTCCG
GCTGCGCGCCTCGGCTTCCACCTGAAAGCCTCGCTGACCGACCGCATCGATGCCAATTTG
GACTACTACCGCGTGTTTGCCCAAAACAAACTCGCCCGCTACGAAACGCGCACGCCCGGA
CACCATATGCTCAACCTCGGCGCAAACTACCGCCGCAATACGCGCTATGGCGAGTGGAAT
TGGTACGTCAAAGCCGACAACCTGCTCAACCAATCCGTTTACGCCCACAGCAGCTTCCTC
TCTGATACGCCACAAATGGGCCGCAGCTTTACCGGTGGCGTAAACGTGAAGTTTTAA

Figure 1B

SEQ ID NO:2

*Neisseria meningitidis* BASB082 polypeptide sequence deduced from the polynucleotide sequence of SEQ ID NO:1

```
MAQTTLKPIVLSILLINTPLLAQAHETEQSVGLETVTVVGKSRPRATSGLLHTSTASDKI
ISGDTLRQKAVNLGDALDGVPGIHASQYGGGASAPVIRGQTGRRIKVLNHHGETGDMADF
SPDHAIMVDTALSQQVEILRGPVTLLYSSGNVAGLVDVADGKIPEKMPENGVSGELGLRL
SSGNLEKLTSGGINIGLGKNFVLHTEGLYRKSGDYAVPRYRNLKRLPDSPRRFANGQHRA
VLGWRKRFYRRTYSDRRDQYGLPAHSHEYDDCHADIIWQKSLINKRYLQLYPHLLTEEDV
DYDNPGLSCGFHDDDDAHAHAHNGKPWIDLRNKRYELRAEWKQPFPGFEALRVHLNRNDY
HHDEKAGDAVENFFNNQTQNARIELRHQPIGRLKGSWGVQYLGQKSSALSATSEAVKQPM
LLDNKVQHYSFFGVEQANWDNFTLEGGVRVEKQKASIRYDKALIDRENYYKQPLPDLGAH
RQTARSFALSGNWYFTPQHKLSLTASHQERLPSTQELYAHGKHVATNTFEVGNKHLNKER
SNNIELALGYEGDRWQYNLALYRNRFGNYIYAQTLNDGRGPKSIEDDSEMKLVRYNQSGA
DFYGAEGEIYFKPTPRYRIGVSGDYVRGRLKNLPSLPGREDAYGNRPFIAQDDQNAPRVP
AARLGFHLKASLTDRIDANLDYYRVFAQNKLARYETRTPGHHMLNLGANYRRNTRYGEWN
WYVKADNLLNQSVYAHSSFLSDTPQMGRSFTGGVNVKF
```

Figure 1C

SEQ ID NO:3

*Neisseria meningitidis* BASB083 polynucleotide sequence from strain ATCC 13090

ATGAAAATATCATTTCATTTAGCTTTATTACCCACGCTGATTATTGCTTCCTTCCCTGTT
GCTGCCGCCGATACGCAGGACAATGGTGAACATTACACCGCCACGCTACCTACCGTTTCC
GTGGTCGGACAGTCCGACACCAGCGTACTCAAAGGCTACATCAACTACGACGAAGCCGCC
GTTACCCGCAACGGACAGCTCATCAAAGAAACGCCGCAAACCATCGATACGCTCAATATC
CAGAAAAACAAAAATTACGGTACGAACGATTTGAGTTCCATCCTCGAAGGCAATGCCGGC
ATCGACGCTGCCTACGATATGCGCGGCGAAAGCATTTTCCTGCGCGGTTTTCAAGCCGAT
GCATCCGATATTTACCGCGACGGCGTGCGCGAAAGCGGACAAGTGCGCCGCAGTACTGCC
AACATCGAGCGCGTGGAAATCCTGAAAGGCCCGTCTTCCGTGCTTTACGGCCGCACCAAC
GGCGGCGGCGTCATCAACATGGTCAGCAAATACGCCAACTTCAAACAAAGCCGCAACATC
GGTGCGGTTTACGGTTCGTGGGCAAACCGCAGCCTGAATATGGACATTAACGAAGTGCTG
AACAAAAACGTCGCCATCCGTCTCACCGGCGAAGTCGGGCGCGCCAATTCGTTCCGCAGC
GGCATAGACAGCAAAAATGTCATGGTTTCACCCAGCATTACCGTCAAACTCGACAACGGC
TTGAAATGGACGGGGCAATACACCTACGACAATGTGGAGCGCACGCCCGACCGCAGTCCG
ACCAAGTCCGTGTACGACCGCTTCGGACTGCCTTACCGCATGGGGTTCGCCCACCGGAAC
GATTTTGTCAAAGACAAGCTGCAAGTTTGGCGTTCCGACCTTGAATACGCCTTCAACGAC
AAATGGCGTGCCCAATGGCAGCTCGCCCACCGCACGGCGGCGCAGGATTTTGATCATTTC
TATGCAGGCAGCGAAAATGGCAACTTAATCAAACGTAACTACGCCTGGCAGCAGACCGAC
AACAAAACCCTGTCGTCCAACTTCACGCTCAACGGCGACTACACCATCGGCCGTTTTGAA
AACCACCTGACCGTAGGCATGGATTACAGCCGCGAACACCGCAACCCGACATTGGGTTTC
AGACGCAACTTTACCGCCTCCATCGATCCATACGACCGCGCAAGCAGGCCGGCTTCGGGC
AGATTGCAGCGTATTCTGGCCCAAGACCGGCACAAAGCCGACTCCTACGGCATCTTCGTG
CAAAACATCTTCTCCGCCACGCCCGATTTGAAATTCGTCCTCGGCGGTCGTTACGACAAG
TACACCTTTAATTCCGAAAACAAACTCACCGGCAGCAGCCGCCAGTACAGCGGACACTCG
TTCAGCCCCAACATCGGTGCAGTGTGGAACATCAATCCCGTCCACACACTTTACGCCTCG
TATAACAAAGCGTTCGCGCCTTATGGCGGACGCGGCGGCTATTTGAGCATCAACACGTCG
TCTTCCGCCGTGTTCAACGCCGACCCCGAGTACACCCGCCAATACGAAACCGGCGTCAAA
AGCAGTTGGCTGGACGACCGCCTCAGCACCACATTGTCCGCCTACCAAATCGAACGCTTC
AATATCCGCTACCGCCCCGACGAGCAAAATGATCCCTACACTTGGGCAGTCGGCGGTAAA
CACCGTTCGCGCGGCGTGGAATTGTCCGCCATCGGGCAAATCATCCCCAAAAAACTCTAT
CTGCGCGGTTCGTTGGGCGTGATGCAGGCGAAAGTCGTTGAAGACAAAAAAAATCCCGAC
CGAGTGGGCATCCATTTGAATAATACCAGCAACGTTACCGGCAACCTGTTTTTCCGTTAT
ACACCGACCGAAAACCTCTACGGCGAAATCGGCGTAACCGGTACAGGCAAACGCTACGGT
TACAACTCAAGAAATAAAGAAGTGACTACGCTTCCAGGCTTTGCCCGAGTTGATGCCATG
CTCGGCTGGAACCATAAAAATGTTAACGTTACCTTTGCCGCAGCCAATCTGTTCAATCAA
AAATATTGGCGTTCGGACTCTATGCCGGGTAATCCGCGCGGCTATACTGCCCGGGTAAAT
TACCGTTTCTGA

SEQ ID NO:4

*Neisseria meningitidis* BASB083 polypeptide sequence deduced from the polynucleotide sequence of SEQ ID NO:3

MKISFHLALLPTLIIASFPVAAADTQDNGEHYTATLPTVSVVGQSDTSVLKGYINYDEAA
VTRNGQLIKETPQTIDTLNIQKNKNYGTNDLSSILEGNAGIDAAYDMRGESIFLRGFQAD
ASDIYRDGVRESGQVRRSTANIERVEILKGPSSVLYGRTNGGGVINMVSKYANFKQSRNI
GAVYGSWANRSLNMDINEVLNKNVAIRLTGEVGRANSFRSGIDSKNVMVSPSITVKLDNG
LKWTGQYTYDNVERTPDRSPTKSVYDRFGLPYRMGFAHRNDFVKDKLQVWRSDLEYAFND
KWRAQWQLAHRTAAQDFDHFYAGSENGNLIKRNYAWQQTDNKTLSSNFTLNGDYTIGRFE
NHLTVGMDYSREHRNPTLGFRRNFTASIDPYDRASRPASGRLQRILAQDRHKADSYGIFV
QNIFSATPDLKFVLGGRYDKYTFNSENKLTGSSRQYSGHSFSPNIGAVWNINPVHTLYAS
YNKAFAPYGGRGGYLSINTSSSAVFNADPEYTRQYETGVKSSWLDDRLSTTLSAYQIERF
NIRYRPDEQNDPYTWAVGGKHRSRGVELSAIGQIIPKKLYLRGSLGVMQAKVVEDKKNPD
RVGIHLNNTSNVTGNLFFRYTPTENLYGEIGVTGTGKRYGYNSRNKEVTTLPGFARVDAM
LGWNHKNVNVTFAAANLFNQKYWRSDSMPGNPRGYTARVNYRF

Figure 1D

SEQ ID NO:5

*Neisseria meningitidis* BASB091 polynucleotide sequence from strain ATCC 13090

GTGAACAAAACCCTCATCCTCGCCCTTTCCGCCCTCCTCGGCCTTGCCGCGTGCAGTGCC
GAACGCGCCTCGCTGTACCCCTCATACAAGCTCAAAGTCATACAGGGCAACGAAATCGAC
CCCCGCGCCGCCGCCGCACTCCGCCTCGGTATGACCAAAGACCAAGTCCTGCTCCTGCTC
GGCAGCCCCCTGTTGCGCGACGCGTTCCACACCGAACGCTGGGACTATACCTTCAACACC
TCCCGCAACGGCATCATCAAAGAACGCAGCAATCTGACCGTCTATTTTGAAAACGGCGTA
CTCGTCCGCACCGAAGGCGACGTCCTGCAAAACGCTGCCGAAGCGCTCAAAGACCGCCAG
AACACAGACAAACCATAA

SEQ ID NO:6

*Neisseria meningitidis* BASB091 polypeptide sequence deduced from the polynucleotide sequence of SEQ ID NO:5

MNKTLILALSALLGLAACSAERASLYPSYKLKVIQGNEIDPRAAAALRLGMTKDQVLLLL
GSPLLRDAFHTERWDYTFNTSRNGIIKERSNLTVYFENGVLVRTEGDVLQNAAEALKDRQ
NTDKP

SEQ ID NO:7

*Neisseria meningitidis* BASB092 polynucleotide sequence from strain ATCC 13090

ATGAAAACCTTCTTCAAAACCCTTTCCGCCGCCGCACTCGCGCTCATCCTCGCCGCCTGC
GGCGGTCAAAAAGACAGCGCGCCCGCCGCATCCGCTTCTGCCGCCGCCGACAACGGCGCG
GAGAAAAAAGAAATCGTCTTCGGCACGACCGTCGGCGACTTCGGCGATATGGTCAAAGAA
CAAATCCAAGCCGAGCTGGAGAAAAAAGGCTACACCGTCAAACTGGTCGAGTTTACCGAC
TATGTACGCCCGAATCTGGCATTGGCTGAGGGCGAGTTGGACATCAACGTCTTCCAACAC
AAACCCTATCTTGACGACTTCAAAAAAGAACACAATCTGGACATCACCGAAGTCTTCCAA
GTGCCGACCGCGCCTTTGGGACTGTACCCGGGCAAGCTGAAATCGCTGGAAGAAGTCAAA
GACGGCAGCACCGTATCCGCGCCCAACGACCCGTCCAACTTCGCCCGCGTCTTGGTGATG
CTCGACGAACTGGGTTGGATCAAACTCAAAGACGGCATCAATCCGCTGACCGCATCCAAA
GCGGACATTGCCGAAAACCTGAAAAACATCAAAATCGTCGAGCTTGAAGCCGCGCAACTG
CCGCGTAGCCGCGCCGACGTGGATTTTGCCGTCGTCAACGGCAACTACGCCATAAGCAGC
GGCATGAAGCTGACCGAAGCCCTGTTCCAAGAACCGAGCTTTGCCTATGTCAACTGGTCT
GCCGTCAAAACCGCCGACAAAGACAGCCAATGGCTTAAAGACGTAACCGAGGCCTATAAC
TCCGACGCGTTCAAAGCCTACGCGCACAAACGCTTCGAGGGCTACAAATCCCCTGCCGCA
TGGAATGAAGGCGCAGCTAAATAA

SEQ ID NO:8

*Neisseria meningitidis* BASB092 polypeptide sequence deduced from the polynucleotide sequence of SEQ ID NO:7

MKTFFKTLSAAALALILAACGGQKDSAPAASASAAADNGAEKKEIVFGTTVGDFGDMVKE
QIQAELEKKGYTVKLVEFTDYVRPNLALAEGELDINVFQHKPYLDDFKKEHNLDITEVFQ
VPTAPLGLYPGKLKSLEEVKDGSTVSAPNDPSNFARVLVMLDELGWIKLKDGINPLTASK
ADIAENLKNIKIVELEAAQLPRSRADVDFAVVNGNYAISSGMKLTEALFQEPSFAYVNWS
AVKTADKDSQWLKDVTEAYNSDAFKAYAHKRFEGYKSPAAWNEGAAK

Figure 1E

SEQ ID NO:9

*Neisseria meningitidis* BASB101 polynucleotide sequence from strain ATCC 13090

GTGAAACCGCGTTTTTATTGGGCAGCCTGCGCCGTCCTGCTGACCGCCTGTTCGCCCGAA
CCTGCCGCCGAAAAAACTGTATCCGCCGCATCCGCATCTGCCGCCACACTGACCGTGCCG
ACCGCGCGGGGCGATGCCGTTGTGCCGAAGAATCCCGAACGCGTCGCCGTGTACGACTGG
GCGGCGTTGGATACGCTGACCGAATTGGGCGTGAATGTGGGCGCAACCACCGCGCCGATG
CGCGTGGATTATTTGCAGCCTGCATTTGACAAGGCGGCAACGGTGGGGACGCTGTTCGAG
CCCGATTACGAAGCCCTGCACCGCTACAATCCTCAGCTTGTCATTACCGGCGGGCCGGGC
GCGGAAGCGTATGAACAGTTGGCGAAAAACGCGACCACCATAGATCTGACGGTGGACAAC
GGCAATATCCGCACCAGCGGCGAAAAGCAGATGGAGACCTTGGCGCGGATTTTCGGCAAG
GAAGCGCGCGCGGCGGAATTGAAGGCGCAGATTGACGCGCTGTTCGCCCAAACGCGCGAA
GCCGCCAAAGGCAAAGGACGCGGGCTGGTGCTGTCGGTTACGGGCAACAAGGTGTCCGCC
TTCGGCACGCAGTCGCGGTTGGCAAGTTGGATACACGGCGACATCGGCCTACCGCCTGTA
GACGAATCTTTACGCAACGAGGGGCACGGGCAGCCTGTTTCCTTCGAATACATCAAAGAG
AAAAACCCCGATTGGATTTTCATCATCGACCGTACCGCCGCCATCGGGCAGGAAGGGCCG
GCGGCTGTCGAAGTATTGGATAACGCGCTGGTACGCGGCACGAACGCTTGGAAGCGCAAG
CAAATCATCGTCATGCCTGCCGCGAACTACATTGTCGCGGGCGGCTCGCGGCAGTTGATT
CAGGCGGCGGAGCAGTTGAAGGCGGCGTTTGAAAAGGCAGAACCCGTTGCGGCGGGGAAA
GAGTAG

SEQ ID NO:10

*Neisseria meningitidis* BASB101 polypeptide sequence deduced from the polynucleotide sequence of SEQ ID NO:9

MKPRFYWAACAVLLTACSPEPAAEKTVSAASASAATLTVPTARGDAVVPKNPERVAVYDW
AALDTLTELGVNVGATTAPMRVDYLQPAFDKAATVGTLFEPDYEALHRYNPQLVITGGPG
AEAYEQLAKNATTIDLTVDNGNIRTSGEKQMETLARIFGKEARAAELKAQIDALFAQTRE
AAKGKGRGLVLSVTGNKVSAFGTQSRLASWIHGDIGLPPVDESLRNEGHGQPVSFEYIKE
KNPDWIFIIDRTAAIGQEGPAAVEVLDNALVRGTNAWKRKQIIVMPAANYIVAGGSRQLI
QAAEQLKAAFEKAEPVAAGKE

BASB082 POLYPEPTIDES

FIELD OF THE INVENTION

This invention relates to polynucleotides, (herein referred to as "BASB082 polynucleotide(s)", "BASB083 polynucleotide(s)", "BASB091 polynucleotide(s)", "BASB092 polynucleotide(s)" and "BASB101 polynucleotide(s)"), polypeptides encoded by them (referred to herein as "BASB082", "BASB083", "BASB091", "BASB092" and "BASB101" respectively or "BASB082 polypeptide(s)", "BASB083 polypeptide(s)", "BASB091 polypeptide(s)", "BASB092 polypeptide(s)" and "BASB101 polypeptide(s)" respectively), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Neisseria meningitidis* (meningococcus) is a Gram-negative bacterium frequently isolated from the human upper respiratory tract. It occasionally causes invasive bacterial diseases such as bacteremia and meningitis. The incidence of N meningococcal disease shows geographical seasonal and annual differences (Schwartz, B., Moore, P. S., Broome, C. V.; Clin. Microbiol. Rev. 2 (Supplement), S18-S24, 1989). Most disease in temperate countries is due to strains of serogroup B and varies in incidence from 1-10/100,000/year total population sometimes reaching higher values (Kaczmarski, E. B. (1997), Commun. Dis. Rep. Rev. 7: R55-9, 1995; Scholten, R. J. P. M., Bijlmer, H. A., Poolman, J. T. et al. Clin. Infect. Dis. 16: 237-246, 1993; Cruz, C., Pavez, G., Aguilar, E., et al. Epidemiol. Infect. 105: 119-126, 1990).

Epidemics dominated by serogroup A meningococci, mostly in central Africa, are encountered, sometimes reaching levels up to 1000/100.000/year (Schwartz, B., Moore, P. S., Broome, C. V. Clin. Microbiol. Rev. 2 (Supplement), S18-S24, 1989). Nearly all cases as a whole of meningococcal disease are caused by serogroup A, B, C, W-135 and Y meningococci and a tetravalent A, C, W-135, Y polysaccharide vaccine is available (Armand, J., Arminjon, F., Mynard, M. C., Lafaix, C., J. Biol. Stand. 10: 335-339, 1982).

The polysaccharide vaccines are currently being improved by way of chemical conjugating them to carrier proteins (Lieberman, J. M., Chiu, S. S., Wong, V. K., et al. JAMA 275: 1499-1503, 1996).

A serogroup B vaccine is not available, since the B capsular polysaccharide was found to be nonimmunogenic, most likely because it shares structural similarity to host components (Wyle, F. A., Artenstein, M. S., Brandt, M. L. et al. J. Infect. Dis. 126: 514-522, 1972; Finne, J. M., Leinonen, M., Makela, P. M. Lancet ii.: 355-357, 1983).

For many years efforts have been initiated and carried out to develop meningococcal outer membrane based vaccines (de Moraes, J. C., Perkins, B., Camargo, M. C. et al. Lancet 340: 1074-1078, 1992; Bjune, G., Hoiby, E. A. Gronnesby, J. K. et al. 338: 1093-1096, 1991). Such vaccines have demonstrated efficacies from 57%-85% in older children (>4 years) and adolescents.

Many bacterial outer membrane components are present in these vaccines, such as PorA, PorB, Rmp, Opc, Opa, FrpB and the contribution of these components to the observed protection still needs futher definition. Other bacterial outer membrane components have been defined by using animal or human antibodies to be potentially relevant to the induction of protective immunity, such as TbpB and NspA (Martin, D., Cadieux, N., Hamel, J., Brodeux, B. R., J. Exp. Med. 185: 1173-1183, 1997; Lissolo, L., Maître-Wilmotte, C., Dumas, p. et al., Inf. Immun. 63: 884-890, 1995). The mechanisms of protective immunity will involve antibody mediated bactericidal activity and opsonophagocytosis.

A bacteremia animal model has been used to combine all antibody mediated mechanisms (Saukkonen, K., Leinonen, M., Abdillahi, H. Poolman, J. T. Vaccine 7: 325-328, 1989). It is generally accepted that the late complement component mediated bactericidal mechanism is crucial for immunity against meningococcal disease (Ross, S. C., Rosenthal P. J., Berberic, H. M., Densen, P. J. Infect. Dis. 155: 1266-1275, 1987).

The frequency of *Neisseria meningitidis* infections has risen dramatically in the past few decades. This has been attributed to the emergence of multiply antibiotic resistant strains and an increasing population of people with weakened immune systems. It is no longer uncommon to isolate *Neisseria meningitidis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB082, BASB083, BASB091, BASB092, and BASB101, in particular BASB082, BASB083, BASB091, BASB092, and BASB101 polypeptides and BASB082, BASB083, BASB091, BASB092, and BASB101 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB082, BASB083, BASB091, BASB092, and BASB101 polynucleotides or polypeptides.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIGS. 1A, 1B, 1C, 1D and 1E show polynucleotide and polypeptide sequences of the invention.

DESCRIPTION OF THE INVENTION

The invention relates to BASB082, BASB083, BASB091, BASB092, and BASB101 polypeptides and polynucleotides as described in greater detail below. The invention relates especially to BASB082, BASB083, BASB091, BASB092, and BASB101 having the nucleotide and amino acid sequences set out in SEQ ID NO: 1,3,5,7,9 and SEQ ID NO:2,4,6,8,10 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Neisseria meningitidis* referred to herein as "BASB082", "BASB083", "BASB091", "BASB092" and "BASB101 " polypeptides", "BASB082 polypeptides", "BASB083 polypeptides", "BASB091 polypeptides", "BASB092 polypeptides", and "BASB101 polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at hleast 85% identity, more preferably at least 90% identity, yet more preferably at least 95% identity, most preferably at least 97-99% or exact identity, to that of SEQ ID NO:2.

(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:1 over the entire length of SEQ ID NO:1.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:2.

The BASB082 polypeptide provided in SEQ ID NO:2 is the BASB082 polypeptides from *Neisseria meningitidis* strains ATCC13090.

The invention also provides an immunogenic fragment of a BASB082 polypeptide, that is, a contiguous portion of the BASB082 polypeptide which has the same or substantially the same immunogenic activity as the polypeptide comprising the amino acid sequence of SEQ ID NO:2. That is to say, the fragment (if necessary when coupled to a carrier) is capable of raising an immune response which recognises the BASB082 polypeptide. Such an immunogenic fragment may include, for example, the BASB082 polypeptide lacking an N-terminal leader sequence, and/or a transmembrane domain and/or a C-terminal anchor domain. In a preferred aspect the immunogenic fragment of BASB082 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:2 over the entire length of SEQ ID NO:2.

The present invention further provides for:

(a) an isolated polypeptide which comprises an amino acid sequence which has at least 85% identity, more preferably at least 90% identity, yet more preferably at least 95% identity, most preferably at least 97-99% or exact identity, to that of SEQ ID NO:4.

(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:3 over the entire length of SEQ ID NO:3.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:4

The BASB083 polypeptide provided in SEQ ID NO:4 is the BASB083 polypeptide from *Neisseria meningitidis* strain ATCC 13090.

The invention also provides an immunogenic fragment of a BASB083 polypeptide, that is, a contiguous portion of the BASB083 polypeptide which has the same or substantially the same immunogenic activity as the polypeptide comprising the amino acid sequence of SEQ ID NO:4. That is to say, the fragment (if necessary when coupled to a carrier) is capable of raising an immune response which recognises the BASB083 polypeptide. Such an immunogenic fragment may include, for example, the BASB083 polypeptide lacking an N-terminal leader sequence, and/or a transmembrane domain and/or a C-terminal anchor domain. In a preferred aspect the immunogenic fragment of BASB083 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:4 over the entire length of SEQ ID NO:4.

The present invention further provides for:

(a) an isolated polypeptide which comprises an amino acid sequence which has at least 85% identity, more preferably at least 90% identity, yet more preferably at least 95% identity, most preferably at least 97-99% or exact identity, to that of SEQ ID NO:6.

(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:5 over the entire length of SEQ ID NO:5.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:6

The BASB091 polypeptide provided in SEQ ID NO:6 is the BASB091 polypeptide from *Neisseria meningitidis* strain ATCC13090.

The invention also provides an immunogenic fragment of a BASB091 polypeptide, that is, a contiguous portion of the BASB091 polypeptide which has the same or substantially the same immunogenic activity as the polypeptide comprising the amino acid sequence of SEQ ID NO:6. That is to say, the fragment (if necessary when coupled to a carrier) is capable of raising an immune response which recognises the BASB091 polypeptide. Such an immunogenic fragment may include, for example, the BASB091 polypeptide lacking an N-terminal leader sequence, and/or a transmembrane domain and/or a C-terminal anchor domain. In a preferred aspect the immunogenic fragment of BASB091 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:6 over the entire length of SEQ ID NO:6.

The present invention further provides for:

(a) an isolated polypeptide which comprises an amino acid sequence which has at least 85% identity, more preferably at least 90% identity, yet more preferably at least 95% identity, most preferably at least 97-99% or exact identity, to that of SEQ ID NO:8.

(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:7 over the entire length of SEQ ID NO:7.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:8

The BASB092 polypeptide provided in SEQ ID NO:8 is the BASB092 polypeptide from *Neisseria meningitidis* strain ATCC13090.

The invention also provides an immunogenic fragment of a BASB092 polypeptide, that is, a contiguous portion of the BASB092 polypeptide which has the same or substantially the same immunogenic activity as the polypeptide comprising the amino acid sequence of SEQ ID NO:8. That is to say, the fragment (if necessary when coupled to a carrier) is capable of raising an immune response which recognises the BASB092 polypeptide. Such an immunogenic fragment may include, for example, the BASB092 polypeptide lacking an N-terminal leader sequence, and/or a transmembrane domain and/or a C-terminal anchor domain. In a preferred aspect the immunogenic fragment of BASB092 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:8 over the entire length of SEQ ID NO:8.

The present invention further provides for:

(a) an isolated polypeptide which comprises an amino acid sequence which has at least 85% identity, more preferably at least 90% identity, yet more preferably at least 95% identity, most preferably at least 97-99% or exact identity, to that of SEQ ID NO:10.

(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:9 over the entire length of SEQ ID NO:9.

(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:10

The BASB101 polypeptide provided in SEQ ID NO:10 is the BASB101 polypeptide from *Neisseria meningitidis* strain ATCC13090.

The invention also provides an immunogenic fragment of a BASB101 polypeptide, that is, a contiguous portion of the BASB101 polypeptide which has the same or substantially the same immunogenic activity as the polypeptide comprising the amino acid sequence of SEQ ID NO:10. That is to say, the fragment (if necessary when coupled to a carrier) is capable of raising an immune response which recognises the BASB101 polypeptide. Such an immunogenic fragment may include, for example, the BASB101 polypeptide lacking an N-terminal leader sequence, and/or a transmembrane domain and/or a C-terminal anchor domain. In a preferred aspect the immunogenic fragment of BASB101 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:10 over the entire length of SEQ ID NO:10.

A fragment is a polypeptide having an amino acid sequence that is entirely the same as part but not all of any amino acid sequence of any polypeptide of the invention. As with BASB082, BASB083, BASB091, BASB092 and BASB101 polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2,4,6,8,10 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2,4,6,8,10 or an isolated polypeptide comprising an amino acid sequence having at least 15, 20, 30, 40, 50 or 100 contiguous amino acids truncated or deleted from the amino acid sequence of SEQ ID NO:2,4,6,8,10.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265-272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795-798}. It is possible to use the repeat portion of the LytA molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Neisseria meningitidis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB082 polypeptides, particularly polynucleotides that encode the polypeptide herein designated BASB082.

In a particularly preferred embodiment of the invention the polynucleotide comprises a region encoding BASB082 polypeptides comprising a sequence set out in SEQ ID NO:1 which includes a full length gene, or a variant thereof.

The BASB082 polynucleotide provided in SEQ ID NO:1 is the BASB082 polynucleotide from *Neisseria meningitidis* strains ATCC13090.

As a further aspect of the invention there are provided isolated nucleic acid molecules encoding and/or expressing BASB082 polypeptides and polynucleotides, particularly *Neisseria meningitidis* BASB082 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB082 polypeptide having a deduced amino acid sequence of SEQ ID NO:2 and polynucleotides closely related thereto and variants thereof.

In another particularly preferred embodiment of the invention there is a BASB082 polypeptide from *Neisseria meningitidis* comprising or consisting of an amino acid sequence of SEQ ID NO:2 or a variant thereof.

Using the information provided herein, such as a polynucleotide sequence set out in SEQ ID NO:1 a polynucleotide of the invention encoding BASB082 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:1 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1 was discovered in a DNA library derived from *Neisseria meningitidis*.

Moreover, each DNA sequence set out in SEQ ID NO:1 contains an open reading frame encoding a protein having about the number of amino acid residues set forth in SEQ ID NO:2 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 2275 of SEQ ID NO:1, encodes the polypeptide of SEQ ID NO:2.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:1 over the entire length of SEQ ID NO:1; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:2 over the entire length of SEQ ID NO:2.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:1 or a fragment thereof; and isolating a full-length gene and/or genomic clones containing said polynucleotide sequence.

The invention provides a polynucleotide sequence identical over its entire length to a coding sequence (open reading frame) in SEQ ID NO:1. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad Sci., USA* 86: 821-824 (1989), or an HA peptide tag (Wilson et al., *Cell* 377: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB082 polypeptide of SEQ ID NO:2 may be identical to the polypeptide encoding sequence contained in nucleotides 1 to 2274 of SEQ ID NO:1. Alternatively it may be a sequence, which as a result of the redundancy (degeneracy) of the genetic code, also encodes the polypeptide of SEQ ID NO:2.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB082 having an amino acid sequence set out in SEQ ID NO:2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2. Fragments of polynucleotides of the invention may be used, for example, to synthesize full-length polynucleotides of the invention.

Further particularly preferred embodiments are polynucleotides encoding BASB082 variants, that have the amino acid sequence of BASB082 polypeptide of SEQ ID NO:2 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB082 polypeptide.

Further preferred embodiments of the invention are polynucleotides that are at least 85% identical over their entire length to a polynucleotide encoding BASB082 polypeptide having an amino acid sequence set out in SEQ ID NO:2 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1.

In accordance with certain preferred embodiments of this invention there are provided polynucleotides that hybridize, particularly under stringent conditions, to BASB082 polynucleotide sequences, such as those polynucleotides in SEQ ID NO:1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB082 and to isolate cDNA and genomic clones of other genes that have a high identity, particularly high sequence identity, to the BASB082 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB082 gene may be isolated by screening using a DNA sequence provided in SEQ ID NO:1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB083 polypeptides, particularly polynucleotides that encode the polypeptide herein designated BASB083.

In a particularly preferred embodiment of the invention the polynucleotide comprises a region encoding BASB083 polypeptides comprising a sequence set out in SEQ ID NO:3 which includes a full length gene, or a variant thereof.

The BASB083 polynucleotide provided in SEQ ID NO:3 is the BASB083 polynucleotide from *Neisseria meningitidis* strains ATCC13090.

As a further aspect of the invention there are provided isolated nucleic acid molecules encoding and/or expressing BASB083 polypeptides and polynucleotides, particularly *Neisseria meningitidis* BASB083 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB083 polypeptide having a deduced amino acid sequence of SEQ ID NO:4 and polynucleotides closely related thereto and variants thereof.

In another particularly preferred embodiment of the invention there is a BASB083 polypeptide from *Neisseria meningitidis* comprising or consisting of an amino acid sequence of SEQ ID NO:4 or a variant thereof.

Using the information provided herein, such as a polynucleotide sequence set out in SEQ ID NO:3 a polynucleotide of the invention encoding BASB083 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:3 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:3 was discovered in a DNA library derived from *Neisseria meningitidis*.

Moreover, each DNA sequence set out in SEQ ID NO:3 contains an open reading frame encoding a protein having about the number of amino acid residues set forth in SEQ ID NO:4 with a deduced molecular weight that can be calculated using amino acid residue molecular weight values well known to those skilled in the art.

The polynucleotide of SEQ ID NO:3, between the start codon at nucleotide number 1 and the stop codon which begins at nucleotide number 2110 of SEQ ID NO:3, encodes the polypeptide of SEQ ID NO:4.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:3 over the entire length of SEQ ID NO:3; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:4 over the entire length of SEQ ID NO:4.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:3 or a fragment thereof; and isolating a full-length gene and/or genomic clones containing said polynucleotide sequence.

The invention provides a polynucleotide sequence identical over its entire length to a coding sequence (open reading frame) in SEQ ID NO:3. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB083 polypeptide of SEQ ID NO:4 may be identical to the polypeptide encoding sequence contained in nucleotides 1 to 2109 of SEQ ID NO:3. Alternatively it may be a sequence, which as a result of the redundancy (degeneracy) of the genetic code, also encodes the polypeptide of SEQ ID NO:4.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB083 having an amino acid sequence set out in SEQ ID NO:4. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:4. Fragments of polynucleotides of the invention may be used, for example, to synthesize full-length polynucleotides of the invention.

Further particularly preferred embodiments are polynucleotides encoding BASB083 variants, that have the amino acid sequence of BASB083 polypeptide of SEQ ID NO:4 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB083 polypeptide.

Further preferred embodiments of the invention are polynucleotides that are at least 85% identical over their entire length to a polynucleotide encoding BASB083 polypeptide having an amino acid sequence set out in SEQ ID NO:4 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:3.

In accordance with certain preferred embodiments of this invention there are provided polynucleotides that hybridize, particularly under stringent conditions, to BASB083 polynucleotide sequences, such as those polynucleotides in SEQ ID NO:3.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, el al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:3 under stringent hybridization conditions with a probe having the sequence of said polynucleotide sequence set forth in SEQ ID NO:3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB083 and-to isolate cDNA and genomic clones of other genes that have a high identity, particularly high sequence identity, to the BASB083 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB083 gene may be isolated by screening using a DNA sequence provided in SEQ ID NO:3 to synthesize an oligonucleotide probe. A labeled oligonucleotide having a sequence complementary to that of a gene of the invention is then used to screen a library of cDNA, genomic DNA or MRNA to determine which members of the library the probe hybridizes to.

It is an object of the invention to provide polynucleotides that encode BASB091 polypeptides, particularly polynucleotides that encode the polypeptide herein designated BASB091.

In a particularly preferred embodiment of the invention the polynucleotide comprises a region encoding BASB091 polypeptides comprising a sequence set out in SEQ ID NO:5 which includes a full length gene, or a variant thereof.

The BASB091 polynucleotide provided in SEQ ID NO:5 is the BASB091 polynucleotide from *Neisseria meningitidis* strains ATCC13090.

As a further aspect of the invention there are provided isolated nucleic acid molecules encoding and/or expressing BASB091 polypeptides and polynucleotides, particularly *Neisseria meningitidis* BASB091 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB091 polypeptide having a deduced amino acid sequence of SEQ ID NO:6 and polynucleotides closely related thereto and variants thereof.

In another particularly preferred embodiment of the invention there is a BASB091 polypeptide from *Neisseria meningitidis* comprising or consisting of an amino acid sequence of SEQ ID NO:6 or a variant thereof.

Using the information provided herein, such as a polynucleotide sequence set out in SEQ ID NO:5 a polynucleotide of the invention encoding BASB091 polypeptide may be obtained using standard cloning and screening methods, such as those for cloning and sequencing chromosomal DNA fragments from bacteria using *Neisseria meningitidis* cells as starting material, following by obtaining a full length clone. For example, to obtain a polynucleotide sequence of the invention, such as a polynucleotide sequence given in SEQ ID NO:5 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:5 was discovered in a DNA library derived from *Neisseria meningitidis*.

Moreover, each DNA sequence set out in SEQ ID NO:5 contains an open reading frame encoding a protein having about the number of amino acid residues set forth in SEQ ID NO:6 with a deduced molecular weight that can be calculated using amino acid residue molecular weight values well known to those skilled in the art.

The polynucleotide of SEQ ID NO:5, between the start codon at nucleotide number 1 and the stop codon which begins at nucleotide number 376 of SEQ ID NO:5, encodes the polypeptide of SEQ ID NO:6.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:5 over the entire length of SEQ ID NO:5; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:6 over the entire length of SEQ ID NO:6.

A polynucleotide encoding a polypeptide of the present invention, including homologs and orthologs from species other than *Neisseria meningitidis,* may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:5 or a fragment thereof; and isolating a full-length gene and/or genomic clones containing said polynucleotide sequence.

The invention provides a polynucleotide sequence identical over its entire length to a coding sequence (open reading frame) in SEQ ID NO:5. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize MRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifing polypeptide sequence fused to them. Polynucleotides of the invention also include, but are not limited to, polynucleotides comprising a structural gene and its naturally associated sequences that control gene expression.

The nucleotide sequence encoding BASB091 polypeptide of SEQ ID NO:6 may be identical to the polypeptide encoding sequence contained in nucleotides 1 to 375 of SEQ ID NO:5. Alternatively it may be a sequence, which as a result of the redundancy (degeneracy) of the genetic code, also encodes the polypeptide of SEQ ID NO:6.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB091 having an amino acid sequence set out in SEQ ID NO:6. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:6. Fragments of polynucleotides of the invention may be used, for example, to synthesize full-length polynucleotides of the invention.

Further particularly preferred embodiments are polynucleotides encoding BASB091 variants, that have the amino acid sequence of BASB091 polypeptide of SEQ ID NO:6 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB091 polypeptide.

Further preferred embodiments of the invention are polynucleotides that are at least 85% identical over their entire length to a polynucleotide encoding BASB091 polypeptide having an amino acid sequence set out in SEQ ID NO:6 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:5.

In accordance with certain preferred embodiments of this invention there are provided polynucleotides that hybridize, particularly under stringent conditions, to BASB091 polynucleotide sequences, such as those polynucleotides in SEQ ID NO:5.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:5 under stringent hybridization conditions with a probe having the sequence of said polynucleotide sequence set forth in SEQ ID NO:5 or a fragment thereof, and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB091 and to isolate cDNA and genomic clones of other genes that have a high identity, particularly high sequence identity, to the BASB091 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB091 gene may be isolated by screening using a DNA sequence provided in SEQ ID NO:5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB092 polypeptides, particularly polynucleotides that encode the polypeptide herein designated BASB092.

In a particularly preferred embodiment of the invention the polynucleotide comprises a region encoding BASB092 polypeptides comprising a sequence set out in SEQ ID NO:7 which includes a full length gene, or a variant thereof.

The BASB092 polynucleotide provided in SEQ ID NO:7 is the BASB092 polynucleotide from *Neisseria meningitidis* strains ATCC13090.

As a further aspect of the invention there are provided isolated nucleic acid molecules encoding and/or expressing BASB092 polypeptides and polynucleotides, particularly *Neisseria meningitidis* BASB092 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB092 polypeptide having a deduced amino acid sequence of SEQ ID NO:8 and polynucleotides closely related thereto and variants thereof.

In another particularly preferred embodiment of the invention there is a BASB092 polypeptide from *Neisseria meningitidis* comprising or consisting of an amino acid sequence of SEQ ID NO:8 or a variant thereof.

Using the information provided herein, such as a polynucleotide sequence set out in SEQ ID NO:7 a polynucleotide of the invention encoding BASB092 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:7 typically a library of clones of chromosomal DNA of

*Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORYMANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:7 was discovered in a DNA library derived from *Neisseria meningitidis.*

Moreover, each DNA sequence set out in SEQ ID NO:7 contains an open reading frame encoding a protein having about the number of amino acid residues set forth in SEQ ID NO:8 with a deduced molecular weight that can be calculated using amino acid residue molecular weight values well known to those skilled in the art.

The polynucleotide of SEQ ID NO:7, between the start codon at nucleotide number 1 and the stop codon which begins at nucleotide number 862 of SEQ ID NO:7, encodes the polypeptide of SEQ ID NO:8.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:7 over the entire length of SEQ ID NO:7; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:8 over the entire length of SEQ ID NO:8.

A polynucleotide encoding a polypeptide of the present invention, including homologs and orthologs from species other than *Neisseria meningitidis,* may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:7 or a fragment thereof; and isolating a full-length gene and/or genomic clones containing said polynucleotide sequence.

The invention provides a polynucleotide sequence identical over its entire length to a coding sequence (open reading frame) in SEQ ID NO:7. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB092 polypeptide of SEQ ID NO:8 may be identical to the polypeptide encoding sequence contained in nucleotides 1 to 861 of SEQ ID NO:7. Alternatively it may be a sequence, which as a result of the redundancy (degeneracy) of the genetic code, also encodes the polypeptide of SEQ ID NO:8.

The termn “polynucleotide encoding a polypeptide” as used herein encompasses polynucleotides that include a sequence encoding a polypeptide of the invention, particularly a bacterial polypeptide and more particularly a polypeptide of the *Neisseria meningitidis* BASB092 having an amino acid sequence set out in SEQ ID NO:8. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:8. Fragments of polynucleotides of the invention may be used, for example, to synthesize full-length polynucleotides of the invention.

Further particularly preferred embodiments are polynucleotides encoding BASB092 variants, that have the amino acid sequence of BASB092 polypeptide of SEQ ID NO:8 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB092 polypeptide.

Further preferred embodiments of the invention are polynucleotides that are at least 85% identical over their entire length to a polynucleotide encoding BASB092 polypeptide having an amino acid sequence set out in SEQ ID NO:8 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:7.

In accordance with certain preferred embodiments of this invention there are provided polynucleotides that hybridize, particularly under stringent conditions, to BASB092 polynucleotide sequences, such as those polynucleotides in SEQ ID NO:7.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:7 under stringent hybridization conditions with a probe having the sequence of said polynucleotide sequence set forth in SEQ ID NO:7 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB092 and to isolate cDNA and genomic clones of other genes that have a high identity, particularly high sequence identity, to the BASB092 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB092 gene may be isolated by screening using a DNA sequence provided in SEQ ID NO:7 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB101 polypeptides, particularly polynucleotides that encode the polypeptide herein designated BASB101.

In a particularly preferred embodiment of the invention the polynucleotide comprises a region encoding BASB101 polypeptides comprising a sequence set out in SEQ ID NO:9 which includes a full length gene, or a variant thereof.

The BASB101 polynucleotide provided in SEQ ID NO:9 is the BASB101 polynucleotide from Neisseria meningitidis strains ATCC13090.

As a further aspect of the invention there are provided isolated nucleic acid molecules encoding and/or expressing BASB101 polypeptides and polynucleotides, particularly Neisseria meningitidis BASB101 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB101 polypeptide having a deduced amino acid sequence of SEQ ID NO:10 and polynucleotides closely related thereto and variants thereof.

In another particularly preferred embodiment of the invention there is a BASB101 polypeptide from Neisseria meningitidis comprising or consisting of an amino acid sequence of SEQ ID NO:10 or a variant thereof.

Using the information provided herein, such as a polynucleotide sequence set out in SEQ ID NO:9 a polynucleotide of the invention encoding BASB101 polypeptide may be obtained using standard cloning and screening methods, such as those for cloning and sequencing chromosomal DNA fragments from bacteria using Neisseria meningitidis cells as starting material, followed by obtaining a full length clone. For example, to obtain a polynucleotide sequence of the invention, such as a polynucleotide sequence given in SEQ ID NO:9 typically a library of clones of chromosomal DNA of Neisseria meningitidis in E. coli or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:9 was discovered in a DNA library derived from Neisseria meningitidis.

Moreover, each DNA sequence set out in SEQ ID NO:9 contains an open reading frame encoding a protein having about the number of amino acid residues set forth in SEQ ID NO:10 with a deduced molecular weight that can be calculated using amino acid residue molecular weight values well known to those skilled in the art.

The polynucleotide of SEQ ID NO:9, between the start codon at nucleotide number 1 and the stop codon which begins at nucleotide number 964 of SEQ ID NO:9, encodes the polypeptide of SEQ ID NO:10.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:9 over the entire length of SEQ ID NO:9; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:10 over the entire length of SEQ ID NO:10.

A polynucleotide encoding a polypeptide of the present invention, including homologs and orthologs from species other than *Neisseria meningitidis,* may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:9 or a fragment thereof, and isolating a full-length gene and/or genomic clones containing said polynucleotide sequence.

The invention provides a polynucleotide sequence identical over its entire length to a coding sequence (open reading frame) in SEQ ID NO:9. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. NatL. Acad. Sci., USA* 86: 821-824 (1989), or an HA peptide tag (Wilson et al, *Cell* 377: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB101 polypeptide of SEQ ID NO:10 may be identical to the polypeptide encoding sequence contained in nucleotides 1 to 963 of SEQ ID NO:9. Alternatively it may be a sequence, which as a result of the redundancy (degeneracy) of the genetic code, also encodes the polypeptide of SEQ ID NO:11.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB101 having an amino acid sequence set out in SEQ ID NO:10. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:10. Fragments of polynucleotides of the invention may be used, for example, to synthesize full-length polynucleotides of the invention.

Further particularly preferred embodiments are polynucleotides encoding BASB101 variants, that have the amino acid sequence of BASB101 polypeptide of SEQ ID NO:10 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB101 polypeptide.

Further preferred embodiments of the invention are polynucleotides that are at least 85% identical over their entire length to a polynucleotide encoding BASB101 polypeptide having an amino acid sequence set out in SEQ ID NO:10 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermnore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:9.

In accordance with certain preferred embodiments of this invention there are provided polynucleotides that hybridize, particularly under stringent conditions, to BASB101 polynucleotide sequences, such as those polynucleotides in SEQ ID NO:9.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCI, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:9 under stringent hybridization conditions with a probe having the sequence of said polynucleotide sequence set forth in SEQ ID NO:9 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB101 and to isolate cDNA and genomic clones of other genes that have a high identity, particularly high sequence identity, to the BASB101 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB101 gene may be isolated by screening using a DNA sequence provided in SEQ ID NO:9 to synthesize an oligonucleotide probe. A labeled oligonucleotide having a sequence complementary to that of a gene of the invention is then used to screen a library of cDNA, genomic DNA or MRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998-9002, 1988). Recent modifications of the technique, exemplified by the MarathonTM technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS: 1-10 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1:363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA,* (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING. A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, E. coli, streptomyces, cyanobacteria, *Bacillus subtilis, Moraxella catarrhalis, Haemophilus influenzae* and *Neisseria meningitidis;* fungal cells, such as cells of a yeast, *Kluveromyces, Saccharomyces,* a basidiomycete, *Candida albicans* and *Aspergillus;* insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picomaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picomaviruses (poliovirus, rhinovirus), herpesviruses (varicella zoster virus, etc), Listeria, Salmonella, Shigella, Neisseria, BCG. These viruses and bacteria can be virulent, or attenuated in various ways in order to obtain live vaccines. Such live vaccines also form part of the invention.

Diagnostic, Prognostic, Serotvping and Mutation Assays

This invention is also related to the use of BASB082, BASB083, BASB091, BASB092 or BASB101 polynucleotides and polypeptides of the invention for use as diagnostic reagents. Detection of BASB082, BASB083, BASB091, BASB092 or BASB101 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB082, BASB083, BASB091, BASB092 or BASB101 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB082, BASB083, BASB091, BASB092 or BASB101 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, VI and SI protection assay or a chemical cleavage method. See, for example, Cotton et al., *Proc. Natl. Acad. Sci., USA,* 85: 4397-4401 (1985).

In another embodiment, an array of oligonucleotides probes comprising BASB082, BASB083, BASB091, BASB092 or BASB101 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science,* 274: 610 (1996)).

Thus in another aspect, the present invention relates to a diagnostic kit which comprises:

(a) a polynucleotide of the present invention, preferably the nucleotide sequence of SEQ ID NO: 1,3,5,7,9 or a fragment thereof;

(b) a nucleotide sequence complementary to that of (a);

(c) a polypeptide of the present invention, preferably the polypeptide of SEQ ID NO:2,4,6,8,10 or a fragment thereof; or (d) an antibody to a polypeptide of the present invention, preferably to the polypeptide of SEQ ID NO:2,4,6,8,10.

It will be appreciated that in any such kit, (a), (b), (c) or (d) may comprise a substantial component. Such a kit will be of use in diagnosing a disease or susceptibility to a disease, among others.

This invention also relates to the use of polynucleotides of the present invention as diagnostic reagents. Detection of a mutated form of a polynucleotide of the invention, preferable, SEQ ID NO: 1,3,5,7,9 which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB082, BASB083, BASB091, BASB092 or BASB101 polypeptide can be used to identify and analyze mutations.

The invention further provides primers with 1, 2, 3 or 4 nucleotides removed from the 5' and/or the 3' end. These primers may be used for, among other things, BASB082, BASB083, BASB091, BASB092 or BASB101 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing disease, preferably bacterial infections, more preferably infections caused by *Neisseria meningitidis*, comprising determining from a sample derived from an individual, such as a bodily material, an increased level of expression of polynucleotide having a sequence of SEQ ID NO: 1,3,5,7,9. Increased or decreased expression of a BASB082, BASB083, BASB091, BASB092 or BASB101 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB082, BASB083, BASB091, BASB092 or BASB101 polypeptide compared to normal control tissue samples may be used to detect the presence of an infection, for example. Assay techniques that can be used to determine levels of a BASB082, BASB083, BASB091, BASB092 or BASBTOI polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probe obtained or derived from a bodily sample, to determine the presence of a particular polynucleotide sequence or related sequence in an individual. Such a presence may indicate the presence of a pathogen, particularly *Neisseria meningitidis,* and may be useful in diagnosing and/or prognosing disease or a course of disease. A grid comprising a number of variants of the polynucleotide sequence of SEQ ID NO: 1,3,5,7,9 are preferred. Also preferred is a grid comprising a number of variants of a polynucleotide sequence encoding the polypeptide sequence of SEQ ID NO:2,4,6,8,10.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB082, BASB083, BASB091, BASB092 or BASB101 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti BASB082, BASB083, BASB091, BASB092 or BASB101 or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB082, BASB083, BASB091, BASB092 or BASB101-polypeptide or BASB082, BASB083, BASB091, BASB092 or BASB101-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarily determining region or regions of the hybridoma-derived antibody has been transplanted into a human monoclonal antibody, for example as described in Jones et al. (1986), *Nature* 321, 522-525 or Tempest et al., (1991) *Biotechnology* 9, 266-273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB082, BASB083, BASB091, BASB092 or BASB101 polypeptide and/or polynucleotide activity in the mixture, and comparing the BASB082, BASB083, BASB091, BASB092 or BASB101 polypeptide and/or polynucleotide activity of the mixture to a standard. Fusion proteins, such as those made from Fc portion and BASB082, BASB083, BASB091, BASB092 or BASB101 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52-58 (1995); and K. Johanson et al., J Biol Chem, 270(16): 9459-9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB082, BASB083, BASB091, BASB092 or BASB101 polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB082, BASB083, BASB091, BASB092 or BASB101 polypeptide and a labeled substrate or ligand of such polypeptide is incubated in the absence or the presence of a candidate molecule that may be a BASB082, BASB083, BASB091, BASB092 or BASB101 agonist or antagonist. The ability of the candidate molecule to agonize or antagonize the BASB082, BASB083, BASB091, BASB092 or BASB101 polypeptide is reflected in decreased binding of the labeled ligand or decreased production of product from such substrate. Molecules that bind gratuitously, i.e., without inducing the effects of BASB082, BASB083, BASB091, BASB092 or BASB101 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB082, BASB083, BASB091, BASB092 or BASB101 polynucleotide or polypeptide activity, and binding assays known in the art.

Another example of an assay for BASB082, BASB083, BASB091, BASB092 or BASB101 agonists is a competitive assay that combines BASB082, BASB083, BASB091, BASB092 or BASB101 and a potential agonist with BASB082, BASB083, BASB091, BASB092 or BASB101-binding molecules, recombinant BASB082, BASB083, BASB091, BASB092 or BASB101 binding molecules, natural substrates or ligands, or substrate or ligand mimetics, under appropriate conditions for a competitive inhibition assay. BASB082, BASB083, BASB091, BASB092 or BASB101 can be labeled, such as by radioactivity or a colorimetric compound, such that the number of BASB082, BASB083, BASB091, BASB092 or BASB101 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB082, BASB083, BASB091, BASB092 or BASB101 -induced activities, thereby preventing the action or expression of BASB082, BASB083, BASB091, BASB092 or BASB101 polypeptides and/or polynucleotides by excluding BASB082, BASB083, BASB091, BASB092 or BASB101 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of BASB082, BASB083, BASB091 or BASB092.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB082, BASB083, BASB091, BASB092 or BASB101 proteins that mediate tissue damage and/or; to block the normal progression of pathogenesis in infections initiated other than by the implantation of in-dwelling devices or by other surgical techniques.

In accordance with yet another aspect of the invention, there are provided BASB082, BASB083, BASB091, BASB092 or BASB101 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB082, BASB083, BASB091, BASB092 or BASB101 polynucleotide and/or polypeptide, or a fragment or variant thereof, adequate to produce antibody and/or T cell immune response to protect said individual from infection, particularly bacterial infection and most particularly *Neisseria meningitidis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB082, BASB083, BASB091, BASB092 or BASB101 polynucleotide and/or polypeptide, or a fragment or a variant thereof, for expressing BASB082, BASB083, BASB091, BASB092 or BASB101 polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB082, BASB083, BASB091, BASB092 or BASB101 polynucleotide and/or polypeptide encoded therefrom, wherein the composition comprises a recombinant BASB082, BASB083, BASB091, BASB092 or BASB101 polynucleotide and/or polypeptide encoded therefrom and/or comprises DNA and/or RNA which encodes and expresses an antigen of said BASB082, BASB083, BASB091, BASB092 or BASB101 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+T cells.

A BASB082, BASB083, BASB091, BASB092 or BASB101 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from Haemophilus influenzae, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

In a vaccine composition according to the invention, a BASB082, BASB083, BASB091, BASB092 or BASB101 polypeptide and/or polynucleotide, or a fragment, or a mimotope, or a variant thereof may be present in a vector, such as the live recombinant vectors described above for example live bacterial vectors.

Also suitable are non-live vectors for the BASB082, BASB083, BASB091, BASB092 or BASB101 polypeptide, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett.* 163:223-228) including *C. trachomatis* and *C. psittaci*. A non-exhaustive list of bacterial pathogens reported to produce blebs also includes: *Bordetella pertussis, Borrelia burgdorferi, Brucella melitensis, Brucella ovis, Esherichia coli, Haemophilus influenza, Legionella pneumophila, Neisseria gonorrhoeae, Neisseria meningitidis, Pseudomonas aeruginosa* and *Yersinia enterocolitica*.

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the BASB082, BASB083, BASB091, BASB092 or BASB101 polypeptide, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the BASB082, BASB083, BASB091, BASB092 or BASB101 gene contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences.

This sequence information allows the modulation of the natural expression of the BASB082, BASB083, BASB091, BASB092 or BASB101 gene. The upregulation of the gene expression may be accomplished by altering the promoter, the shine-dalgarno sequence, potential repressor or operator elements, or any other elements involved. Likewise, downregulation of expression can be achieved by similar types of modification. Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed. In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porb, lbpB, tbpB, p110, 1st, hpuAB from *N. meningitidis* or *N. gonorroheae*; ompCD, copB, lbpB, ompE, UspA1; UspA2; TbpB from *M. Catarrhalis*; p1, p2, p4, p5, p6, IpD, tbpB, D15, Hia, Hmw1, Hmw2 from *H. influenzae*.

In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the BASB082, BASB083, BASB091, BASB092 or BASB101 gene, which modified upstream region contains a heterologous regulatory element which alters the expression level of the BASB082, BASB083, BASB091, BASB092 or BASB101 protein located at the outer membrane. The upstream region according to this aspect of the invention includes the sequence upstream of the BASB082, BASB083, BASB091, BASB092 or BASB101 gene. The upstream region starts immediately upstream of the BASB082, BASB083, BASB091, BASB092 or BASB101 gene and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

Thus, the invention provides a BASB082, BASB083, BASB091, BASB092 and BASB101 polypeptide, in a modified bacterial bleb. The invention further provides modified host cells capable of producing the non-live membrane-based bleb vectors. The invention further provides nucleic acid vectors comprising the BASB082, BASB083, BASB091, BASB092 and BASB101 gene having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. el al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Neisseria meningitidis.* Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Neisseria meningitidis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (*Mosmann, T. R. and Coffnnan, R. L.* (1989) *TH*1 *and TH*2 *cells: different patterns of lymphokine secretion lead to different functional properties. Annual Review of Immunology,* 7,*p*145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2- type responses are associated with the secretion of IL-4, IL-5, IL-6 and IL-13.

It is known that certain vaccine adjuvants are particularly suited to the stimulation of either TH1 or TH2 -type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454). 3D-MPL will be present in the range of 10 µg-100 µg preferably 25-50 µg per dose wherein the antigen will typically be present in a range 2-50 µg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 µg-200 µg, such as 10-100 µg, preferably 10 µg-50 µg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB082, BASB083, BASB091, BASB092 and BASB101 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

The antigen can also be delivered in the form of whole bacteria (dead or alive) or as subcellular fractions, these possibilities do include N. meningitidis itself.

Compositions, Kits and Administration

In a further aspect of the invention there are provided compositions comprising a BASB082, BASB083, BASB091, BASB092 or BASB101 polynucleotide and/or a BASB082, BASB083, BASB091, BASB092 or BASB101 polypeptide for administration to a cell or to a multicellular organism.

The invention also relates to compositions comprising a polynucleotide and/or a polypeptide discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/ or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1-100 μg/μg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

DEFINITIONS

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Mol. Biol.* 215. 403-410 (1990), and FASTA( Pearson and Lipman Proc. Natl. Acad. Sci. USA 85; 2444-2448 (1988). The BLAST family of programs is publicly available from NCBI and other sources (BLAST Manual, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following: Algorithm: Needleman and Wunsch, J. Mol Biol. 48: 443-453 (1970) Comparison matrix: BLOSSUM62 from Henikoff and Henikoff, Proc. Natl. Acad. Sci. USA. 89:10915-10919 (1992)

Gap Penalty: 8

Gap Length Penalty: 2

A program useful with these parameters is publicly available as the "gap" program from Genetics Computer Group, Madison Wis.. The aforementioned parameters are the default parameters for peptide comparisons (along with no penalty for end gaps).

Parameters for polynucleotide comparison include the following:

Algorithm: Needleman and Wunsch, J. Mol Biol. 48: 443-453 (1970)

Comparison matrix: matches=+10, mismatch=0

Gap Penalty: 50

Gap Length Penalty: 3

Available as: The "gap" program from Genetics Computer Group, Madison Wis.

These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO: 1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \circ y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and $\circ$ is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \circ y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., $\circ$ is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \circ y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and ○ is the symbol for the multiplication operator, and wherein any non-integer product of $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \circ y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and ○ is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, upper respiratory tract infection, invasive bacterial diseases, such as bacteremia and meningitis.

EXAMPLES

The examples below are carried out using standard techniques, which are well known and routine to those of skill in the art, except where otherwise described in detail. The examples are illustrative, but do not limit the invention.

Example 1

The BASB082 Gene in *N. Meninaitidis* Strain ATCC 13090

The BASB082 gene of N meningitidis strain ATCC 13090 is shown in SEQ ID NO:1. The translation of the BASB082 polynucleotide sequence, shown in SEQ ID NO:2, shows significant similarity to *Pseudomonas aeruginosa* PhuR, an outer membrane hemin receptor. The BASB082 polypeptide contains a leader signal sequence, as predicted by the program Spscan of the GCG software package. The predicted signal sequence would be cleaved after residue 24. BASB082 is predicted to be an outer membrane protein involved iron uptake.

Example 2

The BASB083 Gene in *N. Menineitidis* strain ATCC 13090

The BASB083 gene of *N. meningitidis* strain ATCC 13090 is shown in SEQ ID NO:3. The translation of the BASB083 polynucleotide sequence, shown in SEQ ID NO:4, shows significant similarity to FhuA, a ferrichrome-iron receptor protein of *Synechocystis* sp.. The BASB083 polypeptide contains a leader signal sequence, as predicted by the program Spscan of the GCG software package. The predicted signal sequence would be cleaved after residue 25. BASB083 is predicted to be an outer membrane protein involved iron uptake.

Example 3

The BASB091 Gene in *N. Menineitidis* Strain ATCC 13090

The BASB091 gene of *N. meningitidis* strain ATCC 13090 is shown in SEQ ID NO:5. The translation of the BASB091 polynucleotide sequence, shown in SEQ ID NO:6, shows significant similarity to *Pseudomonas aeruginosa* OmlA lipoprotein. The BASB091 polypeptide is predicted to contain a lipoprotein signal sequence. The predicted signal sequence would be cleaved after residue 17.

Example 4

The BASB092 Gene in *N. Meninzitidis* Strain ATCC 13090

The BASB092 gene of *N. meningitidis* strain ATCC 13090 is shown in SEQ ID NO:7. The translation of the BASB092 polynucleotide sequence, shown in SEQ ID NO:8, shows significant similarity to *Pasteurella haemolytica* Plp3 lipoprotein. The BASB092 polypeptide is predicted to contain a lipoprotein signal sequence. The predicted signal sequence would be cleaved after residue 19. BASB092 is predicted to be an outer membrane lipoprotein.

Example 5

The BASBIO Gene in *N. Meninaitidis* Strain ATCC 13090

The BASB101 gene of *N. meningitidis* strain ATCC 13090 is shown in SEQ ID NO:9. The translation of the BASB101 polynucleotide sequence, shown in SEQ ID NO:10, shows significant similarity to CeuE, a periplasmic binding protein of an ABC ferrichrome transporter system protein of *Campylobacter coli*. The BASB101 polypeptide contains a lipoprotein signal sequence. The predicted signal sequence would be cleaved after residue 16.

DEPOSITED MATERIALS

A deposit containing a *Neisseria meningitidis* Serogroup B strain has been deposited with the American Type Culture Collection (herein "ATCC") on Jun. 22, 1997 and assigned deposit number 13090. The deposit was described as *Neisseria meningilidis* (Albrecht and Ghon) and is a freeze-dried, 1.5-2.9 kb insert library constructed from *N. meningitidis* isolate. The deposit is described in Int. Bull. Bacteriol. Nomencl. Taxon. 8: 1-15 (1958).

The *Neisseria meningitidis* strain deposit is referred to herein as "the deposited strain" or as "the DNA of the deposited strain."

The deposited strain contains the full length BASB041, 43, 44, 48 genes. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S. C. §112.

What is claimed is:

1. An isolated recombinant polypeptide comprising the amino acid sequence SEQ ID NO:2.

2. The isolated recombinant polypeptide of claim 1, wherein the polypeptide comprises the amino acid sequence SEQ ID NO:2.

3. An isolated recombinant polypeptide comprising an immunogenic fragment of 15 or more contiguous amino acids of SEQ ID NO:2; wherein the immunogenic fragment, when administered to a subject in a suitable composition which can include (a) a co-protein carrier coupled to the recombinant polypeptide or (b) an adjuvant, is capable of inducing an antibody that specifically binds to said fragment within SEQ ID NO:2.

4. The isolated recombinant polypeptide of claim 3, wherein the immunogenic fragment comprises 20 or more contiguous amino acids of SEQ ID NO:2.

5. The isolated recombinant polypeptide of claim 3, wherein the polypeptide is coupled to a co-protein carrier.

6. The isolated recombinant polypeptide of claim 4, wherein the polypeptide is coupled to a co-protein carrier.

7. A fusion protein comprising the isolated recombinant polypeptide of claim 1.

8. A fusion protein comprising the isolated recombinant polypeptide of claim 3.

9. A fusion protein comprising the isolated recombinant polypeptide of claim 4.

10. An immunogenic composition comprising the isolated recombinant polypeptide of claim 1 and a pharmaceutically acceptable carrier.

11. The immunogenic composition of claim 10, wherein the immunogenic composition further comprises at least one other *Neisseria meningitidis* antigen other than a polypeptide comprising SEQ ID NO:2.

12. An immunogenic composition comprising the isolated recombinant polypeptide of claim 3 and a pharmaceutically acceptable carrier.

13. An immunogenic composition comprising the isolated recombinant polypeptide of claim 4 and a pharmaceutically acceptable carrier.

14. An immunogenic composition comprising the fusion protein of claim 7 and a pharmaceutically acceptable carrier.

15. An immunogenic composition comprising the fusion protein of claim 8 and a pharmaceutically acceptable carrier.

16. An immunogenic composition comprising the fusion protein of claim 9 and a pharmaceutically acceptable carrier.

17. The immunogenic composition of claim 10, further comprising an adjuvant.

18. The immunogenic composition of claim 12, further comprising an adjuvant.

19. The immunogenic composition of claim 13, further comprising an adjuvant.

20. The immunogenic composition of claim 14, further comprising an adjuvant.

21. The immunogenic composition of claim 15, further comprising an adjuvant.

22. The immunogenic composition of claim 16, further comprising an adjuvant.

23. A method for inducing an antibody in a mammal comprising administering the isolated recombinant polypeptide of claim 1 to the mammal in an amount effective to induce an antibody.

* * * * *

UNITED STATES PATENT AND TRADEMARK OFFICE
CERTIFICATE OF CORRECTION

PATENT NO. : 7,666,988 B1  Page 1 of 1
APPLICATION NO. : 09/936377
DATED : February 23, 2010
INVENTOR(S) : Catherine Defrenne et al.

It is certified that error appears in the above-identified patent and that said Letters Patent is hereby corrected as shown below:

Column 65
Line 49, "2. The isolated recombinant polypeptide of claim 1, wherein the polypeptide comprises the amino acid sequence SEQ ID NO: 2." should read -- 2. The isolated recombinant polypeptide of claim 1, wherein the isolated recombinant polypeptide consists of SEQ ID NO: 2. --.

Signed and Sealed this

Second Day of November, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 2277
<212> TYPE: DNA
<213> ORGANISM: Neisseria meningitidis

<400> SEQUENCE: 1
atggcacaaa ctacactcaa acccattgtt ttatcaattc ttttaatcaa cacacccctc     60
ctcgcccaag cgcatgaaac tgagcaatcg gtgggcttgg aaacggttac cgtcgtcggc    120
aaaagccgtc cgcgcgccac atcagggctg ctgcacactt cgaccgcctc cgacaaaatc    180
atcagcggcg acaccttgcg acaaaaagcc gtcaacttgg gcgatgcttt ggacggcgtg    240
ccgggcattc acgcctcgca atacggcggc ggcgcgtccg ctcccgttat tcgcggtcaa    300
acaggcagac ggattaaagt attgaaccat cacggcgaaa caggcgatat ggcggatttt    360
tcgcccgatc acgccattat ggtagatacc gccttgtcgc aacaggtcga aatcctgcgc    420
gggccggtta cgctcttgta cagctcgggc aatgtggcgg ggctggtcga tgttgccgat    480
ggcaaaatcc ccgaaaaaat gcctgaaaac ggcgtatcgg gcgaactcgg attgcgtttg    540
agcagcggca atctggaaaa actcacgtcc ggcggcatca atatcggttt gggcaaaaac    600
tttgtattgc acacggaagg gctgtaccgc aaatcggggg attacgccgt accgcgttac    660
cgcaatctga aacgcctgcc cgacagccca cgccgattcg caaacgggca gcatcgggct    720
gtcttgggtt ggcgaaaaag gttttatcgg cgtacgtaca gcgaccgtcg cgaccaatat    780
ggtctgcctg cccacagcca cgaatacgat gattgccacg ccgacatcat ctggcaaaag    840
agcttgatta acaaacgcta tttacagctt tatccgcacc tgttgaccga agaagacgtc    900
gattacgaca atccgggctt gagctgcggc ttccacgacg acgatgatgc acacgcccat    960
```

-continued

```
gcccacaacg gcaaaccttg gatagacctg cgcaacaaac gctacgaact ccgcgccgaa    1020
tggaagcagc cattccccgg ttttgaagcc ctgcgcgtac acctgaaccg caacgactac    1080
caccacgacg aaaaagcagg cgatgcagtc gaaaactttt ttaacaacca aacgcaaaac    1140
gcccgcatcg agttgcgcca ccaacccata ggccgtctga aggcagctg  gggcgtgcaa    1200
tatttgggac aaaaatccag tgctttatct gccacatccg aagcggtcaa caaccgatg    1260
ctgcttgaca ataaagtgca acattacagc tttttcggtg tagaacaggc aaactgggac    1320
aacttcacgc ttgaaggcgg cgtacgcgtg gaaaaacaaa aagcctccat ccgctacgac    1380
aaagcattga ttgatcggga aaactactac aagcagcccc tgcccgacct cggcgcgcac    1440
cgccaaaccg cccgctcgtt cgcactttcg ggcaactggt atttcacgcc gcaacacaaa    1500
ctcagcctga ccgcctccca tcaggaacgc ctgccgtcaa cgcaagagct gtacgcacac    1560
ggcaaacacg ttgccaccaa cacttttgaa gtcggcaaca acacctgaa  caaagagcgt    1620
tccaacaaca tcgaactcgc gttgggctac gaaggcgacc gctggcaata caatctggca    1680
ctctaccgca accgcttcgg caactacatt tacgcccaaa ccttaaacga cggacgcggc    1740
cccaaatcca tcgaagacga cagcgaaatg aagctcgtgc gctacaacca atccggtgcg    1800
gacttctacg gcgcggaagg cgaaatctac ttcaaaccga caccgcgcta ccgcatcggc    1860
gtttccggcg actatgtacg aggccgtctg aaaaacctgc cgtccctacc cggcagggaa    1920
gatgcctacg gcaaccgtcc tttcatcgcg caggacgacc aaaacgcccc tcgcgttccg    1980
gctgcgcgcc tcggcttcca cctgaaagcc tcgctgaccg accgcatcga tgccaatttg    2040
gactactacc gcgtgtttgc ccaaaacaaa ctcgcccgct acgaaacgcg cacgcccgga    2100
caccatatgc tcaacctcgg cgcaaactac cgccgcaata cgcgctatgg cgagtggaat    2160
tggtacgtca agccgacaa  cctgctcaac caatccgttt acgcccacag cagcttcctc    2220
tctgatacgc cacaaatggg ccgcagcttt accggtggcg taaacgtgaa gttttaa       2277
```

<210> SEQ ID NO 2
<211> LENGTH: 758
<212> TYPE: PRT
<213> ORGANISM: Neisseria meningitidis

<400> SEQUENCE: 2

```
Met Ala Gln Thr Thr Leu Lys Pro Ile Val Leu Ser Ile Leu Leu Ile
  1               5                  10                  15

Asn Thr Pro Leu Leu Ala Gln Ala His Glu Thr Glu Gln Ser Val Gly
             20                  25                  30

Leu Glu Thr Val Thr Val Val Gly Lys Ser Arg Pro Arg Ala Thr Ser
         35                  40                  45

Gly Leu Leu His Thr Ser Thr Ala Ser Asp Lys Ile Ile Ser Gly Asp
     50                  55                  60

Thr Leu Arg Gln Lys Ala Val Asn Leu Gly Asp Ala Leu Asp Gly Val
 65                  70                  75                  80

Pro Gly Ile His Ala Ser Gln Tyr Gly Gly Gly Ala Ser Ala Pro Val
                 85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140
```

-continued

```
Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser Pro Arg Phe Ala Asn Gly Gln His Arg Ala
225                 230                 235                 240

Val Leu Gly Trp Arg Lys Arg Phe Tyr Arg Arg Thr Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285

Gln Leu Tyr Pro His Leu Leu Thr Glu Glu Asp Val Asp Tyr Asp Asn
    290                 295                 300

Pro Gly Leu Ser Cys Gly Phe His Asp Asp Asp Ala His Ala His
305                 310                 315                 320

Ala His Asn Gly Lys Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
            340                 345                 350

Val His Leu Asn Arg Asn Asp Tyr His His Asp Glu Lys Ala Gly Asp
        355                 360                 365

Ala Val Glu Asn Phe Phe Asn Asn Gln Thr Gln Asn Ala Arg Ile Glu
    370                 375                 380

Leu Arg His Gln Pro Ile Gly Arg Leu Lys Gly Ser Trp Gly Val Gln
385                 390                 395                 400

Tyr Leu Gly Gln Lys Ser Ser Ala Leu Ser Ala Thr Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
        435                 440                 445

Arg Val Glu Lys Gln Lys Ala Ser Ile Arg Tyr Asp Lys Ala Leu Ile
    450                 455                 460

Asp Arg Glu Asn Tyr Tyr Lys Gln Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560
```

-continued

```
Leu Tyr Arg Asn Arg Phe Gly Asn Tyr Ile Tyr Ala Gln Thr Leu Asn
            565                 570                 575
Asp Gly Arg Gly Pro Lys Ser Ile Glu Asp Asp Ser Glu Met Lys Leu
        580                 585                 590
Val Arg Tyr Asn Gln Ser Gly Ala Asp Phe Tyr Gly Ala Glu Gly Glu
    595                 600                 605
Ile Tyr Phe Lys Pro Thr Pro Arg Tyr Arg Ile Gly Val Ser Gly Asp
610                 615                 620
Tyr Val Arg Gly Arg Leu Lys Asn Leu Pro Ser Leu Pro Gly Arg Glu
625                 630                 635                 640
Asp Ala Tyr Gly Asn Arg Pro Phe Ile Ala Gln Asp Gln Asn Ala
            645                 650                 655
Pro Arg Val Pro Ala Ala Arg Leu Gly Phe His Leu Lys Ala Ser Leu
        660                 665                 670
Thr Asp Arg Ile Asp Ala Asn Leu Asp Tyr Tyr Arg Val Phe Ala Gln
    675                 680                 685
Asn Lys Leu Ala Arg Tyr Glu Thr Arg Thr Pro Gly His His Met Leu
690                 695                 700
Asn Leu Gly Ala Asn Tyr Arg Arg Asn Thr Arg Tyr Gly Glu Trp Asn
705                 710                 715                 720
Trp Tyr Val Lys Ala Asp Asn Leu Leu Asn Gln Ser Val Tyr Ala His
            725                 730                 735
Ser Ser Phe Leu Ser Asp Thr Pro Gln Met Gly Arg Ser Phe Thr Gly
        740                 745                 750
Gly Val Asn Val Lys Phe
        755
```

```
<210> SEQ ID NO 3
<211> LENGTH: 2112
<212> TYPE: DNA
<213> ORGANISM: Neisseria meningitidis

<400> SEQUENCE: 3
atgaaaatat catttcattt agctttatta cccacgctga ttattgcttc cttccctgtt      60
gctgccgccg atacgcagga caatggtgaa cattacaccg ccacgctacc taccgtttcc     120
gtggtcggac agtccgacac cagcgtactc aaaggctaca tcaactacga cgaagccgcc     180
gttacccgca acggacagct catcaaagaa cgccgcaaa ccatcgatac gctcaatatc      240
cagaaaaaca aaaattacgg tacgaacgat ttgagttcca tcctcgaagg caatgccggc     300
atcgacgctg cctacgatat gcgcggcgaa agcatttttcc tgcgcggttt tcaagccgat     360
gcatccgata tttaccgcga cggcgtgcgc gaaagcggac aagtgcgccg cagtactgcc     420
aacatcgagc gcgtggaaat cctgaaaggc ccgtcttccg tgctttacgg ccgcaccaac     480
ggcggcggcg tcatcaacat ggtcagcaaa tacgccaact caaacaaag ccgcaacatc      540
ggtgcggttt acggttcgtg ggcaaaccgc agcctgaata tggacattaa cgaagtgctg     600
aacaaaaacg tcgccatccg tctcaccggc gaagtcgggc gcgccaattc gttccgcagc     660
ggcatagaca gcaaaaatgt catggtttca cccagcatta ccgtcaaact cgacaacggc     720
ttgaaatgga cggggcaata cacctacgac aatgtggagc gcacgcccga ccgcagtccg     780
accaagtccg tgtacgaccg cttcggactg ccttaccgca tggggttcgc ccaccggaac     840
gattttgtca agacaagct gcaagtttgg cgttccgacc ttaatacgc cttcaacgac      900
aaatggcgtg cccaatggca gctcgcccac cgcacggcgg cgcaggattt tgatcatttc     960
```

-continued

```
tatgcaggca gcgaaaatgg caacttaatc aaacgtaact acgcctggca gcagaccgac     1020
aacaaaaccc tgtcgtccaa cttcacgctc aacggcgact acaccatcgg ccgttttgaa     1080
aaccacctga ccgtaggcat ggattacagc cgcgaacacc gcaacccgac attgggtttc     1140
agacgcaact ttaccgcctc catcgatcca tacgaccgcg caagcaggcc ggcttcgggc     1200
agattgcagc gtattctggc caagaccgga cacaaagccg actcctacgg catcttcgtg     1260
caaaacatct tctccgccac gcccgatttg aaattcgtcc tcggcggtcg ttacgacaag     1320
tacaccttta attccgaaaa caaactcacc ggcagcagcc gccagtacag cggacactcg     1380
ttcagcccca acatcggtgc agtgtggaac atcaatcccg tccacacact ttacgcctcg     1440
tataacaaag cgttcgcgcc ttatggcgga cgcggcggct atttgagcat caacacgtcg     1500
tcttccgccg tgttcaacgc cgaccccgag tacacccgcc aatacgaaac cggcgtcaaa     1560
agcagttggc tggacgaccg cctcagcacc acattgtccg cctaccaaat cgaacgcttc     1620
aatatccgct accgccccga cgagcaaaat gatccctaca cttgggcagt cggcggtaaa     1680
caccgttcgc gcggcgtgga attgtccgcc atcgggcaaa tcatccccaa aaaactctat     1740
ctgcgcggtt cgttgggcgt gatgcaggcg aaagtcgttg aagacaaaaa aaatcccgac     1800
cgagtgggca tccatttgaa taataccagc aacgttaccg gcaacctgtt tttccgttat     1860
acaccgaccg aaaacctcta cggcgaaatc ggcgtaaccg gtacaggcaa acgctacggt     1920
tacaactcaa gaaataaaga agtgactacg cttccaggct ttgcccgagt tgatgccatg     1980
ctcggctgga accataaaaa tgttaacgtt acctttgccg cagccaatct gttcaatcaa     2040
aaatattggc gttcggactc tatgccgggt aatccgcgcg gctatactgc ccgggtaaat     2100
taccgtttct ga                                                         2112
```

<210> SEQ ID NO 4
<211> LENGTH: 703
<212> TYPE: PRT
<213> ORGANISM: Neisseria meningitidis

<400> SEQUENCE: 4

```
Met Lys Ile Ser Phe His Leu Ala Leu Leu Pro Thr Leu Ile Ile Ala
 1               5                  10                  15

Ser Phe Pro Val Ala Ala Ala Asp Thr Gln Asp Asn Gly Glu His Tyr
            20                  25                  30

Thr Ala Thr Leu Pro Thr Val Ser Val Gly Gln Ser Asp Thr Ser
        35                  40                  45

Val Leu Lys Gly Tyr Ile Asn Tyr Asp Glu Ala Ala Val Thr Arg Asn
    50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
```

-continued

```
                165                 170                 175
Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
            195                 200                 205

Thr Gly Glu Val Gly Arg Ala Asn Ser Phe Arg Ser Gly Ile Asp Ser
            210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
                260                 265                 270

Arg Met Gly Phe Ala His Arg Asn Asp Phe Val Lys Asp Lys Leu Gln
                275                 280                 285

Val Trp Arg Ser Asp Leu Glu Tyr Ala Phe Asn Asp Lys Trp Arg Ala
            290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Phe Thr Leu Asn Gly
                340                 345                 350

Asp Tyr Thr Ile Gly Arg Phe Glu Asn His Leu Thr Val Gly Met Asp
                355                 360                 365

Tyr Ser Arg Glu His Arg Asn Pro Thr Leu Gly Phe Arg Arg Asn Phe
            370                 375                 380

Thr Ala Ser Ile Asp Pro Tyr Asp Arg Ala Ser Arg Pro Ala Ser Gly
385                 390                 395                 400

Arg Leu Gln Arg Ile Leu Ala Gln Asp Arg His Lys Ala Asp Ser Tyr
                405                 410                 415

Gly Ile Phe Val Gln Asn Ile Phe Ser Ala Thr Pro Asp Leu Lys Phe
                420                 425                 430

Val Leu Gly Gly Arg Tyr Asp Lys Tyr Thr Phe Asn Ser Glu Asn Lys
            435                 440                 445

Leu Thr Gly Ser Ser Arg Gln Tyr Ser Gly His Ser Phe Ser Pro Asn
            450                 455                 460

Ile Gly Ala Val Trp Asn Ile Asn Pro Val His Thr Leu Tyr Ala Ser
465                 470                 475                 480

Tyr Asn Lys Ala Phe Ala Pro Tyr Gly Gly Arg Gly Gly Tyr Leu Ser
                485                 490                 495

Ile Asn Thr Ser Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
            515                 520                 525

Ser Thr Thr Leu Ser Ala Tyr Gln Ile Glu Arg Phe Asn Ile Arg Tyr
            530                 535                 540

Arg Pro Asp Glu Gln Asn Asp Pro Tyr Thr Trp Ala Val Gly Gly Lys
545                 550                 555                 560

His Arg Ser Arg Gly Val Glu Leu Ser Ala Ile Gly Gln Ile Pro
                565                 570                 575

Lys Lys Leu Tyr Leu Arg Gly Ser Leu Gly Val Met Gln Ala Lys Val
            580                 585                 590
```

Val Glu Asp Lys Lys Asn Pro Asp Arg Val Gly Ile His Leu Asn Asn
            595                 600                 605

Thr Ser Asn Val Thr Gly Asn Leu Phe Phe Arg Tyr Thr Pro Thr Glu
        610                 615                 620

Asn Leu Tyr Gly Glu Ile Gly Val Thr Gly Thr Gly Lys Arg Tyr Gly
625                 630                 635                 640

Tyr Asn Ser Arg Asn Lys Glu Val Thr Thr Leu Pro Gly Phe Ala Arg
                645                 650                 655

Val Asp Ala Met Leu Gly Trp Asn His Lys Asn Val Asn Val Thr Phe
            660                 665                 670

Ala Ala Ala Asn Leu Phe Asn Gln Lys Tyr Trp Arg Ser Asp Ser Met
        675                 680                 685

Pro Gly Asn Pro Arg Gly Tyr Thr Ala Arg Val Asn Tyr Arg Phe
    690                 695                 700

<210> SEQ ID NO 5
<211> LENGTH: 378
<212> TYPE: DNA
<213> ORGANISM: Neisseria meningitidis

<400> SEQUENCE: 5
gtgaacaaaa ccctcatcct cgcccttcc gccctcctcg gccttgccgc gtgcagtgcc    60
gaacgcgcct cgctgtaccc ctcatacaag ctcaaagtca tacagggcaa cgaaatcgac   120
ccccgcgccg ccgccgcact ccgcctcggt atgaccaaag accaagtcct gctcctgctc   180
ggcagccccc tgttgcgcga cgcgttccac accgaacgct gggactatac cttcaacacc   240
tcccgcaacg gcatcatcaa agaacgcagc aatctgaccg tctatttga aaacggcgta   300 ctcgtccgca ccgaaggcga cgtcctgcaa aacgctgccg aagcgctcaa agaccgccag   360
aacacagaca aaccataa                                                 378

<210> SEQ ID NO 6
<211> LENGTH: 125
<212> TYPE: PRT
<213> ORGANISM: Neisseria meningitidis

<400> SEQUENCE: 6

Met Asn Lys Thr Leu Ile Leu Ala Leu Ser Ala Leu Leu Gly Leu Ala
 1               5                  10                  15

Ala Cys Ser Ala Glu Arg Ala Ser Leu Tyr Pro Ser Tyr Lys Leu Lys
            20                  25                  30

Val Ile Gln Gly Asn Glu Ile Asp Pro Arg Ala Ala Ala Ala Leu Arg
        35                  40                  45

Leu Gly Met Thr Lys Asp Gln Val Leu Leu Leu Gly Ser Pro Leu
    50                  55                  60

Leu Arg Asp Ala Phe His Thr Glu Arg Trp Asp Tyr Thr Phe Asn Thr
65                  70                  75                  80

Ser Arg Asn Gly Ile Ile Lys Glu Arg Ser Asn Leu Thr Val Tyr Phe
                85                  90                  95

Glu Asn Gly Val Leu Val Arg Thr Glu Gly Asp Val Leu Gln Asn Ala
            100                 105                 110

Ala Glu Ala Leu Lys Asp Arg Gln Asn Thr Asp Lys Pro
        115                 120                 125

<210> SEQ ID NO 7
<211> LENGTH: 864

```
<212> TYPE: DNA
<213> ORGANISM: Neisseria meningitidis

<400> SEQUENCE: 7
atgaaaacct tcttcaaaac cctttccgcc gccgcactcg cgctcatcct cgccgcctgc      60
ggcggtcaaa agacagcgc ccccgccgca tccgcttctg ccgccgccga caacggcgcg     120
gagaaaaaag aaatcgtctt cggcacgacc gtcggcgact cggcgatat ggtcaaagaa     180
caaatccaag ccgagctgga aaaaaaggc tacaccgtca aactggtcga gtttaccgac     240
tatgtacgcc cgaatctggc attggctgag ggcgagttgg acatcaacgt cttccaacac     300
aaaccctatc ttgacgactt caaaaaagaa cacaatctgg acatcaccga gtcttccaa      360
gtgccgaccg cgcctttggg actgtacccg gcaagctga atcgctgga agaagtcaaa      420
gacggcagca ccgtatccgc gcccaacgac ccgtccaact tcgcccgcgt cttggtgatg     480
ctcgacgaac tgggttggat caaactcaaa gacggcatca atccgctgac cgcatccaaa     540
gcggacattg ccgaaaacct gaaaaacatc aaaatcgtcg agcttgaagc cgcgcaactg     600
ccgcgtagcc gcgccgacgt ggattttgcc gtcgtcaacg gcaactacgc cataagcagc     660
ggcatgaagc tgaccgaagc cctgttccaa gaaccgagct ttgcctatgt caactggtct     720
gccgtcaaaa ccgccgacaa agacagccaa tggcttaaag acgtaaccga ggcctataac     780
tccgacgcgt tcaaagccta cgcgcacaaa cgcttcgagg gctacaaatc ccctgccgca     840
tggaatgaag gcgcagctaa ataa                                             864

<210> SEQ ID NO 8
<211> LENGTH: 287
<212> TYPE: PRT
<213> ORGANISM: Neisseria meningitidis

<400> SEQUENCE: 8

Met Lys Thr Phe Phe Lys Thr Leu Ser Ala Ala Leu Ala Leu Ile
 1               5                  10                  15

Leu Ala Ala Cys Gly Gly Gln Lys Asp Ser Ala Pro Ala Ala Ser Ala
            20                  25                  30

Ser Ala Ala Ala Asp Asn Gly Ala Glu Lys Lys Glu Ile Val Phe Gly
        35                  40                  45

Thr Thr Val Gly Asp Phe Gly Asp Met Val Lys Glu Gln Ile Gln Ala
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190
```

```
Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285
```

<210> SEQ ID NO 9
<211> LENGTH: 966
<212> TYPE: DNA
<213> ORGANISM: Neisseria meningitidis

<400> SEQUENCE: 9

```
gtgaaaccgc gttttattg  ggcagcctgc gccgtcctgc tgaccgcctg ttcgcccgaa    60
cctgccgccg aaaaaactgt atccgccgca tccgcatctg ccgccacact gaccgtgccg   120
accgcgcggg gcgatgccgt tgtgccgaag aatcccgaac gcgtcgccgt gtacgactgg   180
gcggcgttgg atacgctgac cgaattgggc gtgaatgtgg gcgcaaccac cgcgccgatg   240
cgcgtggatt atttgcagcc tgcatttgac aaggcggcaa cggtggggac gctgttcgag   300
cccgattacg aagccctgca ccgctacaat cctcagcttg tcattaccgg cgggccgggc   360
gcggaagcgt atgaacagtt ggcgaaaaac gcgaccacca tagatctgac ggtgacaac    420
ggcaatatcc gcaccagcgg cgaaaagcag atggagacct ggcgcggat tttcggcaag   480
gaagcgcgcg cggcggaatt gaaggcgcag attgacgcgc tgttcgccca aacgcgcgaa   540
gccgccaaag gcaaaggacg cgggctggtg ctgtcggtta cgggcaacaa ggtgtccgcc   600
ttcggcacgc agtcgcggtt ggcaagttgg atacacggcg acatcggcct accgcctgta   660
gacgaatctt tacgcaacga ggggcacggg cagcctgttt ccttcgaata catcaaagag   720
aaaaaccccg attggatttt catcatcgac cgtaccgccg ccatcgggca ggaagggccg   780
gcggctgtcg aagtattgga taacgcgctg gtacgcggca cgaacgcttg gaagcgcaag   840
caaatcatcg tcatgcctgc cgcgaactac attgtcgcgg gcggctcgcg gcagttgatt   900
caggcggcg  agcagttgaa ggcggcgttt gaaaaggcag aacccgttgc ggcggggaaa   960
gagtag                                                              966
```

<210> SEQ ID NO 10
<211> LENGTH: 321
<212> TYPE: PRT
<213> ORGANISM: Neisseria meningitidis

<400> SEQUENCE: 10

```
Met Lys Pro Arg Phe Tyr Trp Ala Ala Cys Ala Val Leu Leu Thr Ala
1               5                   10                  15

Cys Ser Pro Glu Pro Ala Ala Glu Lys Thr Val Ser Ala Ala Ser Ala
            20                  25                  30

Ser Ala Ala Thr Leu Thr Val Pro Thr Ala Arg Gly Asp Ala Val Val
        35                  40                  45

Pro Lys Asn Pro Glu Arg Val Ala Val Tyr Asp Trp Ala Ala Leu Asp
    50                  55                  60
```

-continued

```
Thr Leu Thr Glu Leu Gly Val Asn Val Gly Ala Thr Thr Ala Pro Met
 65                  70                  75                  80

Arg Val Asp Tyr Leu Gln Pro Ala Phe Asp Lys Ala Ala Thr Val Gly
                 85                  90                  95

Thr Leu Phe Glu Pro Asp Tyr Glu Ala Leu His Arg Tyr Asn Pro Gln
            100                 105                 110

Leu Val Ile Thr Gly Gly Pro Gly Ala Glu Ala Tyr Glu Gln Leu Ala
            115                 120                 125

Lys Asn Ala Thr Thr Ile Asp Leu Thr Val Asp Asn Gly Asn Ile Arg
            130                 135                 140

Thr Ser Gly Glu Lys Gln Met Glu Thr Leu Ala Arg Ile Phe Gly Lys
145                 150                 155                 160

Glu Ala Arg Ala Ala Glu Leu Lys Ala Gln Ile Asp Ala Leu Phe Ala
                165                 170                 175

Gln Thr Arg Glu Ala Ala Lys Gly Lys Gly Arg Gly Leu Val Leu Ser
            180                 185                 190

Val Thr Gly Asn Lys Val Ser Ala Phe Gly Thr Gln Ser Arg Leu Ala
            195                 200                 205

Ser Trp Ile His Gly Asp Ile Gly Leu Pro Pro Val Asp Glu Ser Leu
    210                 215                 220

Arg Asn Glu Gly His Gly Gln Pro Val Ser Phe Glu Tyr Ile Lys Glu
225                 230                 235                 240

Lys Asn Pro Asp Trp Ile Phe Ile Ile Asp Arg Thr Ala Ala Ile Gly
                245                 250                 255

Gln Glu Gly Pro Ala Ala Val Glu Val Leu Asp Asn Ala Leu Val Arg
            260                 265                 270

Gly Thr Asn Ala Trp Lys Arg Lys Gln Ile Ile Val Met Pro Ala Ala
            275                 280                 285

Asn Tyr Ile Val Ala Gly Gly Ser Arg Gln Leu Ile Gln Ala Ala Glu
            290                 295                 300

Gln Leu Lys Ala Ala Phe Glu Lys Ala Glu Pro Val Ala Ala Gly Lys
305                 310                 315                 320

Glu
```